United States Patent
Mizumoto

(10) Patent No.: US 8,894,930 B2
(45) Date of Patent: Nov. 25, 2014

(54) SPECIMEN PROCESSING DEVICE AND SPECIMEN PROCESSING METHOD

(75) Inventor: Toru Mizumoto, Kobe (JP)

(73) Assignee: Sysmex Corporation (JP)

(*) Notice: Subject to any disclaimer, the term of this patent is extended or adjusted under 35 U.S.C. 154(b) by 342 days.

(21) Appl. No.: 12/788,001

(22) Filed: May 26, 2010

(65) Prior Publication Data

US 2010/0300217 A1 Dec. 2, 2010

(30) Foreign Application Priority Data

May 29, 2009 (JP) ................. 2009-130428
May 29, 2009 (JP) ................. 2009-130470

(51) Int. Cl.
*G01N 35/02* (2006.01)
*G01N 15/14* (2006.01)
*G01N 35/00* (2006.01)
*G01N 35/10* (2006.01)

(52) U.S. Cl.
CPC ............ *G01N 15/14* (2013.01); *G01N 35/0092* (2013.01); *G01N 35/10* (2013.01)
USPC ................ 422/67; 422/68.1; 422/65; 422/63; 422/81; 422/509; 422/518; 436/43; 436/47; 436/50

(58) Field of Classification Search
CPC . G01N 35/10; G01N 35/00584; G01N 35/02; G01N 35/0092
USPC ......... 422/63–67, 68.1, 81, 509, 518; 436/43, 436/47, 50
See application file for complete search history.

(56) References Cited

U.S. PATENT DOCUMENTS

| | | | | |
|---|---|---|---|---|
| 4,113,436 A | * | 9/1978 | Werder et al. | 422/65 |
| 4,861,553 A | * | 8/1989 | Mawhirt et al. | 422/65 |
| 5,114,681 A | * | 5/1992 | Bertoncini et al. | 422/111 |
| 5,139,744 A | * | 8/1992 | Kowalski | 422/67 |
| 5,773,662 A | * | 6/1998 | Imai et al. | 436/50 |
| 5,885,530 A | * | 3/1999 | Babson et al. | 422/65 |
| 5,966,309 A | * | 10/1999 | O'Bryan et al. | 700/225 |
| 6,090,630 A | | 7/2000 | Koakutsu et al. | |
| 6,556,923 B2 | * | 4/2003 | Gallagher et al. | 702/23 |
| 6,694,197 B1 | * | 2/2004 | Hatcher et al. | 700/56 |
| 7,105,132 B2 | * | 9/2006 | Shumate et al. | 422/510 |
| 8,322,510 B2 | * | 12/2012 | Pedrazzini | 198/346.2 |
| 2003/0215362 A1 | * | 11/2003 | Sato et al. | 422/63 |

(Continued)

FOREIGN PATENT DOCUMENTS

| | | |
|---|---|---|
| JP | 06-160397 A | 6/1994 |
| JP | 06-207943 A | 7/1994 |
| JP | 10-142230 A | 5/1998 |
| JP | 2003-121449 A | 4/2003 |

(Continued)

*Primary Examiner* — Brian R Gordon
(74) *Attorney, Agent, or Firm* — Brinks Gilson & Lione

(57) ABSTRACT

A specimen processing device is disclosed that comprises: a processing unit configured to aspirate a specimen from a specimen container accommodating the specimen, and to process the aspirated specimen; a state transition section configured to make the processing unit undergo transition to a pause state; an instruction accepting section configured to accept an instruction to start processing of the specimen when the processing unit is in the pause state; and a pause state releasing section configured to release the processing unit from the pause state to make the processing unit perform the processing of specimen when the instruction to start the processing is accepted by the instruction accepting section. A specimen processing method using a specimen processing device is also disclosed.

25 Claims, 18 Drawing Sheets

(56) References Cited

U.S. PATENT DOCUMENTS

| | | |
|---|---|---|
| 2003/0220761 A1 | 11/2003 | Biwa |
| 2004/0091396 A1* | 5/2004 | Nakamura et al. ............... 422/65 |
| 2005/0036913 A1* | 2/2005 | Yamakawa et al. ............. 422/65 |
| 2009/0082984 A1 | 3/2009 | Wakamiya et al. |
| 2010/0196202 A1* | 8/2010 | Talmer et al. ................... 422/63 |

FOREIGN PATENT DOCUMENTS

| | | |
|---|---|---|
| JP | 2003-232797 A | 8/2003 |
| JP | 2004-045396 A | 2/2004 |
| JP | 3725961 B2 | 12/2005 |
| JP | 2008-281454 A | 11/2008 |
| JP | 2009-074887 A | 4/2009 |

* cited by examiner

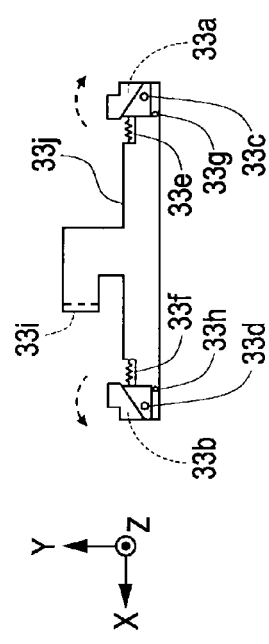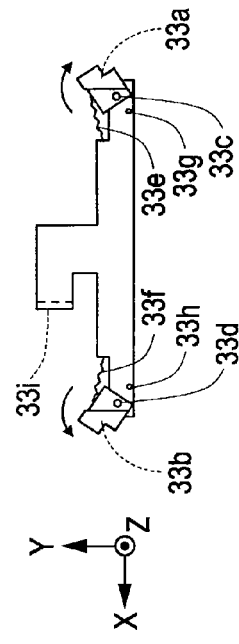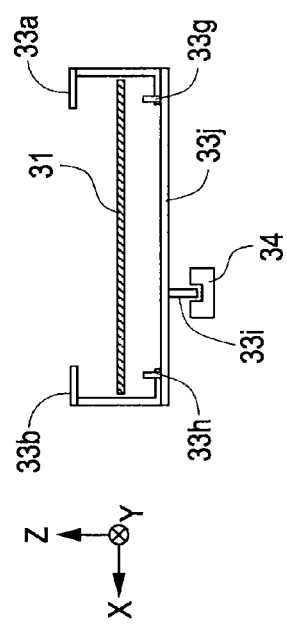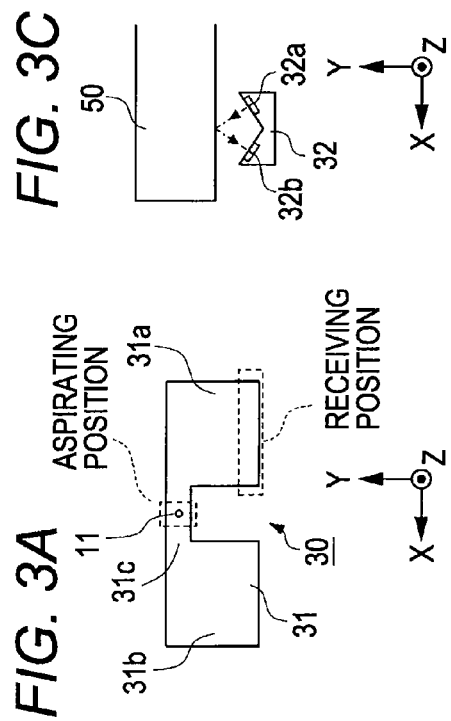

SPECIMEN PROCESSING DEVICE AND SPECIMEN PROCESSING METHOD

RELATED APPLICATIONS

This application claims priority from Japanese Patent Application Nos. 2009-130428 and 2009-130470 both filed on May 29, 2009. The disclosures of the above applications are herein incorporated by reference in their entirety.

BACKGROUND OF THE INVENTION

1. Field of the Invention

The present invention relates to a specimen processing device and a specimen processing method for performing a predetermined process such as examination and analysis on a specimen such as urine and blood.

2. Description of the Related Art

The specimen processing device for processing specimens such as urine and blood is used in medical facilities such as hospitals. Some specimen processing devices transport the specimen aspirated from a specimen container to each unit using a pneumatic source.

This type of specimen processing device may have a function of making the device undergo transition to an inactivated state to suppress power consumption (e.g., Japanese Laid-Open Patent Publication No. 2003-121449). In the inactivated state, current flow other than to the configuring portions that need to maintain current flow such as a reagent refrigerating compartment and a control unit is stopped. The release of the inactivated state is executed by the input of a startup instruction from a user to an operation unit, or by the registration of patient information to a higher-order system. The specimen starts to be analyzed when the user selects a start button after the inactivated state is released and a preparation operation of the specimen processing device is completed.

In the specimen processing device described above, a predetermined preparation operation such as startup of the pneumatic source is performed to have the device in a processable state when the startup instruction for releasing the inactivated state is input from the user or when the patient information is registered to the higher-order system. It normally takes a few minutes until the preparation operation is completed. The user needs to instruct the start of processing of the specimen by selecting the start button after waiting for the preparation operation to be completed.

If such a preparation period occurs, the user tends to carry out other works in the meantime. However, once the user starts to carry out other works, the user may be deeply involved in the other works and may not notice that the preparation has completed, and thus may thereafter leave the specimen processing device in non-operation. In this case, the specimen processing device again returns to the inactivated state although it has undergone transition to the activated state. When the user returns to the specimen processing device after finishing the other works, the specimen processing device may have already returned to the inactivated state. The user thus needs to re-input the startup instruction to release the inactivated state.

Thus, lowering of work efficiency in medical coding is a concern in the conventional release method. Considering the current situation of the medical facilities, it is not highly preferable to wait for the preparation period to finish without carrying out other works in front of the specimen processing device.

When releasing a pause by registering the patient information to the higher-order system, a long time is required from when the patient information is registered until the process is actually performed in the specimen processing device, and there is a problem in which wasteful power consumption arises in the meantime. Steps such as blood drawing and centrifugal separation are often carried out after the patient information is registered in the higher-order system, and a long period is required until the processing in the specimen processing device is performed. Thus, wasteful power consumption arises before processes are started on the specimen if the pause state is released by registration of the patient information.

In view of such problems, it is an object of the present invention to provide a specimen processing device capable of suppressing power consumption while simplifying the operation of the user.

SUMMARY OF THE INVENTION

The scope of the present invention is defined solely by the appended claims, and is not affected to any degree by the statements within this summary.

A first specimen processing device embodying features of the present invention includes: a processing unit configured to aspirate a specimen from a specimen container accommodating the specimen, and to process the aspirated specimen; a state transition section configured to make the processing unit undergo transition to a pause state; an instruction accepting section configured to accept an instruction to start processing of the specimen when the processing unit is in the pause state; and a pause state releasing section configured to release the processing unit from the pause state to make the processing unit perform the processing of specimen when the instruction to start the processing is accepted by the instruction accepting section.

A second specimen processing device embodying features of the present invention includes: a processing unit configured to aspirate a specimen from a specimen container accommodating the specimen, and to process the aspirated specimen; and a control unit configured to control the operation of the processing unit; wherein the control unit makes the processing unit undergo transition to a pause state, accepts an instruction to start processing of the specimen when the processing unit is in the pause state, and releases the processing unit from the pause state to make the processing unit perform the processing of specimen when the instruction to start the processing is accepted.

A third specimen processing device embodying features of the present invention includes: a conveyance unit configured to convey a specimen container accommodating a specimen to an aspirating position; a processing unit configured to aspirate the specimen from the specimen container conveyed to the aspirating position, and to process the aspirated specimen; a state transition section configured to make the processing unit undergo transition to a pause state; a detection unit for detecting existence of the specimen container at a predetermined position on a conveyance path on which the conveyance unit conveys the specimen container to the aspirating position; and a pause releasing section for releasing the processing unit from the pause state based on the detection of the existence of the specimen container by the detection unit.

A fourth specimen processing device embodying features of the present invention includes: a conveyance unit configured to convey a specimen container accommodating a specimen to a predetermined position; a processing unit for acquiring the specimen container conveyed to the predetermined position, aspirating the specimen from the specimen container, and processing the aspirated specimen; a state transition section configured to make the processing unit undergo transition to a pause state; a detection unit configured to detect existence of the specimen container at a second predetermined position on a conveyance path on which the conveyance unit conveys the specimen container to the predetermined position; and a pause releasing section configured to release the processing unit from the pause state based on the detection of the existence of the specimen container by the detection unit.

A fifth specimen processing device embodying features of the present invention includes: a conveyance unit configured to convey a specimen container accommodating a specimen to an aspirating position; a processing unit configured to aspirate the specimen from the specimen container conveyed to the aspirating position, and to process the aspirated specimen; a control unit configured to control the processing unit; and a detection unit configured to detect existence of the specimen container at a predetermined position on a conveyance path on which the conveyance unit conveys the specimen container to the aspirating position; wherein the control unit, makes the processing unit undergo transition to a pause state, and releases the processing unit from the pause state based on the detection of the existence of the specimen container by the detection unit.

A first specimen processing method using a specimen processing device including a processing unit configured to process a specimen, embodying features of the present invention includes steps of: making the processing unit undergo transition to a pause state; accepting an instruction to start processing of the specimen when the processing unit is in the pause state; and releasing the processing unit from the pause state to make the processing unit perform the processing of specimen when the instruction to start the processing by the processing unit is accepted; wherein each step is automatically executed by the specimen processing device.

The effects and significance of the present invention should become apparent from the description on the embodiments below. It should be recognized that the embodiments described below are merely illustrations in implementing the present invention, and the present invention is not to be limited to the following embodiments in any manner.

BRIEF DESCRIPTION OF THE DRAWINGS

FIG. 3A is a view for describing the configuration of the conveyance device according to the first embodiment;

FIG. 3B is a view for describing the configuration of the conveyance device according to the first embodiment;

FIG. 3C is a view for describing the configuration of the conveyance device according to the first embodiment;

FIG. 3D is a view for describing the configuration of the conveyance device according to the first embodiment;

FIG. 3E is a view for describing the configuration of the conveyance device according to the first embodiment;

FIG. 3F is a view for describing the configuration of the conveyance device according to the first embodiment;

DETAILED DESCRIPTION OF THE PREFERRED EMBODIMENTS

In the present embodiment, the present invention is applied to a clinical specimen examination apparatus for examining red blood cells, white blood cells, epidermal cells, and the like (examination of urinary sediment) contained in urine. Such examinations are performed on the specimen that further requires urinary sediment examination as a result of examinations on urinary protein, glucose in urine, and the like (examination of urinary qualitative). In the present embodiment, a plurality of specimen containers for accommodating different specimens is set in a rack, and each specimen is examined after the rack is set in the specimen examination apparatus.

1. First Embodiment

The specimen examination apparatus according to a first embodiment will be described below with reference to the figures. In the present embodiment, the rack is set in the specimen examination apparatus by the hand of the user.

Figure 1:
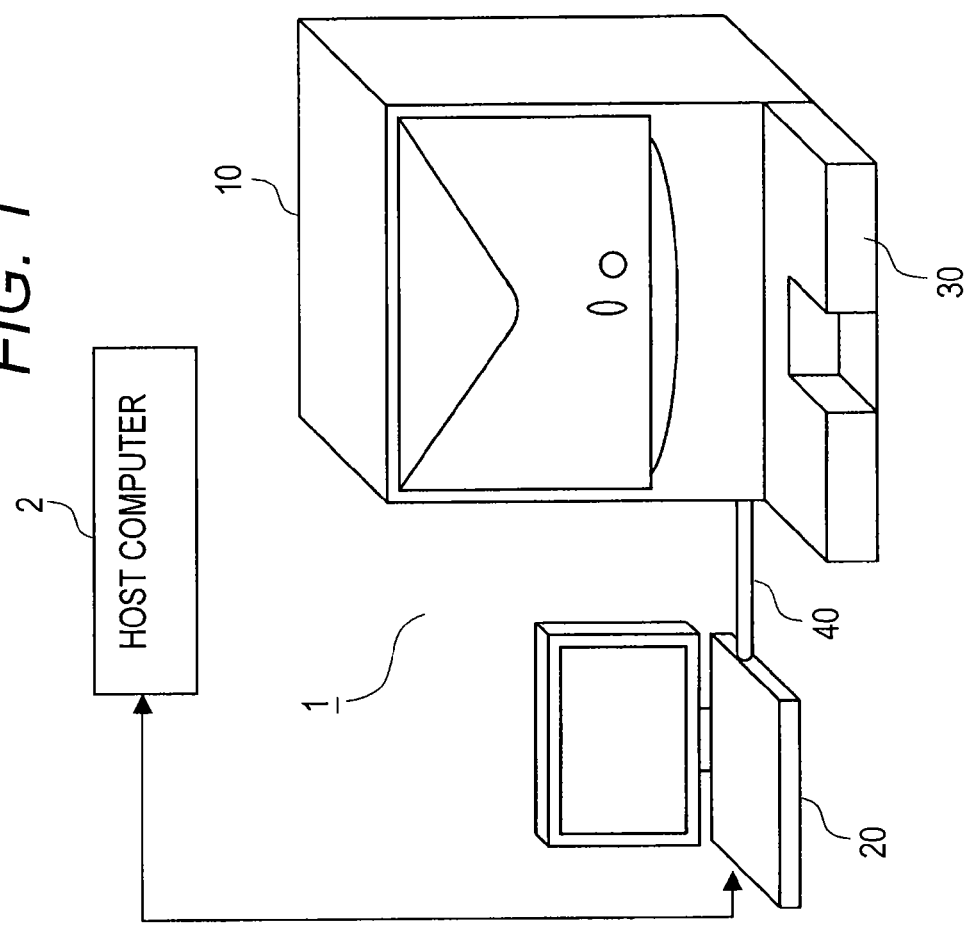
FIG. 1 is a view showing a configuration of a specimen examination system according to a first embodiment.

FIG. 1 is a view showing a configuration of an entire system including a specimen examination apparatus 1. The specimen examination apparatus 1 according to the present embodiment includes a measurement device 10, an information processing device 20, and a conveyance device 30. In the embodiment of the figure, the measurement device 10 and the information processing device 20 are connected with a cable 40, but the information processing device 20 may be incorporated in the measurement device 10.

Figure 2:
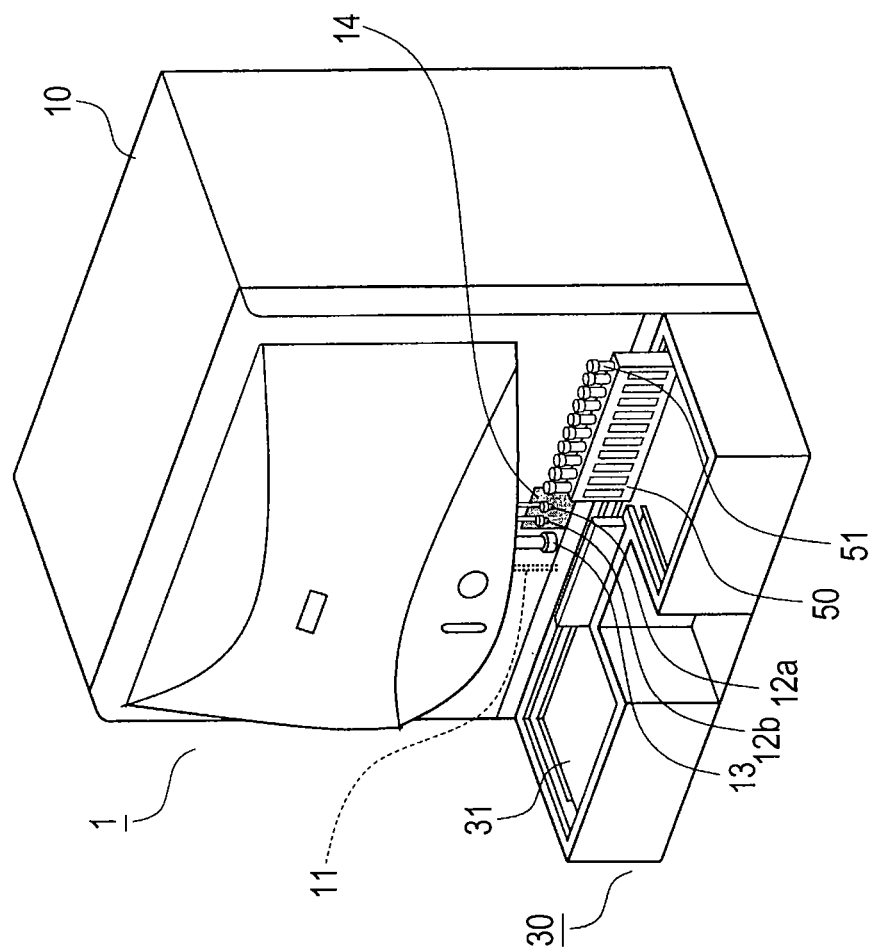
FIG. 2 is a view showing an outer appearance configuration of a measurement device and a conveyance device according to the first embodiment.

FIG. 2 is a perspective view of an outer appearance of the measurement device 10 and the conveyance device 30. The measurement device 10 includes a nozzle 11, rotators 12a, 12b, a rotation supporter 13, and a barcode reader 14. The conveyance device 30 is attached to the front surface of the measurement device 10, and includes a conveyance path 31. A rack 50 accommodates a plurality of specimen containers 51. A barcode label for specifying the specimen is attached to the side surface of each specimen container 51.

The bottom surface of the conveyance path 31 is configured by a metal flat plate. The plurality of specimen containers accommodated in the rack 50 are conveyed onto the conveyance path 31 by a rack pushing mechanism section and a rack transverse feeding mechanism section of the conveyance device 30. The rack pushing mechanism section and the rack transverse feeding mechanism section of the conveyance device 30 will be described later with reference to FIGS. 3 and 4.

The nozzle 11 aspirates the specimen from the specimen container 51 at an aspirating position of the conveyance path 31. During the aspirating operation, the nozzle 11 is moved to the position, indicated with a broken line in the figure, from the measurement device 10 and driven in the up and down direction at the relevant position so as to be inserted and removed with respect to the specimen container 51 at the aspirating position. The rotators 12a, 12b and the rotation supporter 13 include an anti-slip member of circular column shape. The rotators 12a, 12b and the rotation supporter 13 sandwich the specimen container 51 at the position facing the barcode reader 14 from the direction of the side surfaces, and rotate the specimen container 51 in the circumferential direction in the rack 50. The barcode attached to the side surface of the specimen container is thereby faced to the barcode reader 14. The barcode reader 14 reads the barcode attached to the side surface of the specimen container 51. The rotators 12a, 12b, the rotation supporter 13, and the barcode reader 14 will be described later with reference to FIGS. 3 and 4.

FIG. 3 is a view showing the conveyance device 30. FIGS. 3A and 3B are plan views when the conveyance path 31 and the conveyance device 30 are seen from the upper side, and FIG. 3C is a plan view when the rack 50 and a portion of a sensor 32 are seen from the upper side. FIGS. 3D to 3F are views showing a configuration of a rack pushing mechanism section 33.

With reference to FIG. 3A, the conveyance path 31 includes a right bath region 31a and a left bath region 31b, which right bath region 31a and left bath region 31b are coupled by a coupling region 31c. The specimen is aspirated from the specimen container 51 at the position (aspirating position) facing the nozzle 11 at the middle of the coupling region 31c. A position (hereinafter referred to as "receiving position") for setting the specimen container 51 is set on the most nearside position (end positioning the negative direction of the Y axis) of the right bath region 31a. Since the rack 50 accommodates the plurality of specimen containers 51 in the transverse direction (X axis direction), the receiving position of each specimen container 51 lines in a row in the transverse direction (X axis direction).

The configuration of the conveyance device 30 will be described with reference to FIG. 3B.

The conveyance device 30 includes, in addition to the conveyance path 31, the sensor 32, the rack pushing mechanism section 33, a photo-interrupter 34, a switch 35, a transverse feeding mechanism section 36, a switch 37, and a rack pushing mechanism section 38. In the figure, the nozzle 11, the rotators 12a, 12b, the rotation supporter 13, and the barcode reader 14 are also illustrated for the sake of convenience.

The sensor 32 determines whether or not the specimen container 51 is set at the receiving position. As shown in FIG. 3C, the sensor 32 includes a light emitting portion 32a and a light receiving portion 32b. If the rack 50 is set at the receiving position, the light from the light emitting portion 32a is reflected by the side surface of the rack 50, and received by the light receiving portion 32b. If the rack 50 is not set at the receiving position, the light from the light emitting portion 32a is not received by the light receiving portion 32b. The presence of the rack 50 (specimen container 51) at the receiving position can be detected in such a manner.

Returning back to FIG. 3B, the rack pushing mechanism section 33 is positioned on the back side of the conveyance path 31, and is driven in the positive direction of the Y axis. The rack pushing mechanism section 33 includes projections 33a, 33b for pushing the rack 50 in the positive direction of the Y axis. Furthermore, the rack pushing mechanism section 33 includes a shielding portion (not shown) to be inserted to a gap (detection gap) between the light emitting portion and the light receiving portion of the photo-interrupter 34 at the position in the figure. When the rack pushing mechanism section 33 is driven in the positive direction of the Y axis, the rack 50 is pushed by the projections 33a, 33b so that the right bath region 31a is moved in the positive direction of the Y axis. The configuration of the rack pushing mechanism section 33 will be described later with reference to FIGS. 3D to 3F.

The photo-interrupter 34 determines whether or not the rack pushing mechanism section 33 is at the most nearside position (position of the rack pushing mechanism section 33 shown in the figure). In other words, the rack pushing mechanism section 33 is detected to be at the most nearside position if the shielding portion of the rack pushing mechanism section 33 is in the detection gap of the photo-interrupter 34. The photo-interrupter 34 will be described later with reference to FIG. 3F.

The switch 35 detects whether or not the rack 50 is at the most back side of the right bath region 31a. In other words, when the rack 50 that is pushed in the positive direction of the Y axis is moved to the most back side of the right bath region 31a by the rack pushing mechanism section 33, the switch 35 is pushed by the side surface in the positive direction of the Y axis of the rack 50. Detection is thus made that the rack 50 reached the most back side of the right bath region 31a.

The transverse feeding mechanism section 36 includes projections 36a, 36b that rotate about an axis parallel to the Y axis. The projections 36a, 36b slightly project out from the upper surface of the conveyance path 31 in a predetermined rotation stroke, and moves from right to left (positive direction of X axis) along the conveyance path 31. In this case, when the projection gets caught at the bottom surface of the rack 50, the rack 50 at the most back side of the right bath region 31a is moved towards the left (positive direction of X axis), and moved to the most back side of the left bath region 31b through the coupling region 31c.

The switch 37 detects whether or not the rack 50 is at the most back side of the left bath region 31b. In other words, when the rack 50 is moved to the most back side of the left bath region 31b by the rack pushing mechanism section 36, the switch 37 is pushed by the side surface in the positive direction of the X axis of the rack 50. Detection is thus made that the rack 50 reached the most back side of the left bath region 31b.

The rack pushing mechanism section 38 moves in the Y axis direction in the left bath region 31b of the conveyance path 31. The rack 50 at the most back side of the left bath region 31b is pushed out in the negative direction of the Y axis when the rack pushing mechanism section 38 is driven in the positive direction of the Y axis.

The configuration of the rack pushing mechanism section 33 will now be described.

With reference to FIG. 3D, the rack pushing mechanism section 33 includes, in addition to the projections 33a, 33b, rotation shafts 33c, 33d, springs 33e, 33f, stoppers 33g, 33h, a shielding portion 33i, and a base plate 33j.

The projections 33a, 33b are rotatably attached to the base plate 33j by way of the rotation shafts 33c, 33d. The projections 33a, 33b are respectively biased in the counterclockwise direction and the clockwise direction by the springs 33e, 33f, and are pushed against the stoppers 33g, 33h.

The projections 33a, 33b do not rotate even if a force in the negative direction of the Y axis is applied on the projections 33a, 33b from the state of the figure. If, however, a force in the positive direction of the Y axis is applied on the projections 33a, 33b from the state of the figure, the projections 33a, 33b respectively rotate in the clockwise direction and the counterclockwise direction against the bias of the springs 33e, 33f, as shown in FIG. 3E.

FIG. 3F is a view of the rack pushing mechanism section 33 seen from the negative direction of the Y axis. The projections 33a, 33b are positioned on the upper side (positive direction of Z axis) than the bottom surface of the conveyance path 31, and the base plate 33j is positioned on the lower side (negative direction of Z axis) than the bottom surface of the conveyance path 31.

The shielding portion 33i arranged at the lower surface of the base plate 33j. As described above, the shielding portion 33i is positioned in the detection gap of the photo-interrupter 34 when the rack pushing mechanism section 33 is at the most nearside position. Detection is thus made that the rack pushing mechanism section 33 is at the most nearside position from the output of the photo-interrupter 34.

Figure 4A:
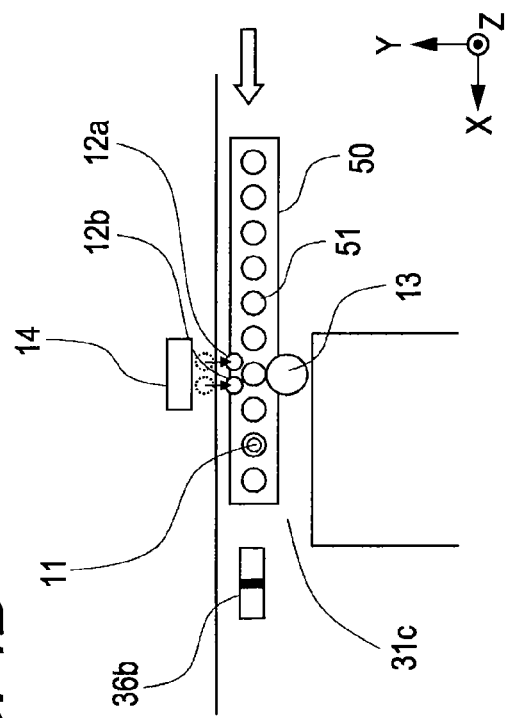
FIG. 4A is a view for describing the conveyance operation of a specimen container according to the first embodiment.
Figure 4B:
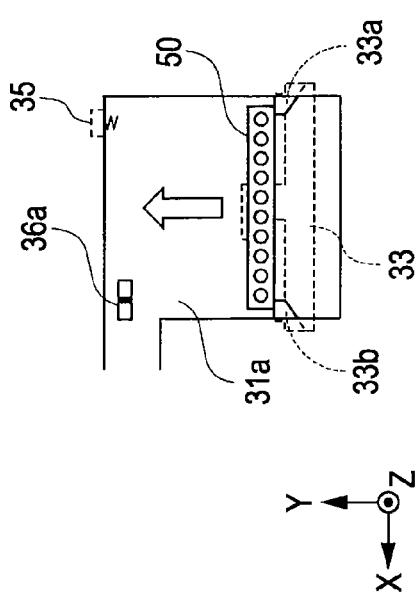
FIG. 4B is a view for describing the conveyance operation of a specimen container according to the first embodiment.
Figure 4C:
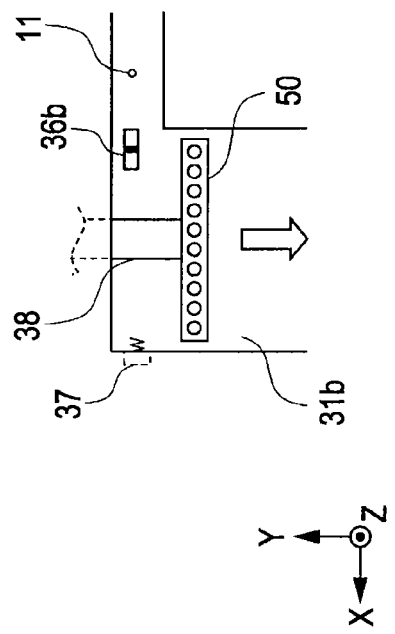
FIG. 4C is a view for describing the conveyance operation of a specimen container according to the first embodiment.

FIG. 4 is a view showing a conveyance operation of the rack 50. FIGS. 4A to 4C are respectively plan views showing the movement operation of the rack 50 in the right bath region 31a, the coupling region 31c, and the left bath region 31b.

With reference to FIG. 4A, the side surface on the near side of the rack 50 is pushed by the projections 33a, 33b of the rack pushing mechanism section 33, so that the rack 50 is moved in the positive direction of the Y axis. The rack pushing mechanism section 33 pushes the rack 50 to the most back side of the right bath region 31a, and again returns to the most nearside position. If another rack 50 is present in the right bath region 31a, the other rack 50 contacts the projections 33a, 33b in the middle of the movement. In this case, however, the rack pushing mechanism section 33 can smoothly return to the most nearside position since the projections 33a, 33b rotate against the springs 33e, 33f, as shown in FIG. 3E.

With reference to FIG. 4B, the rack 50 conveyed in such a manner is then moved in the left direction (positive direction of X axis) through the coupling region 31c by the projections 36a, 36b of the transverse feeding mechanism section 36 (not shown in the figure). When the specimen container 51 reaches the position facing the barcode reader 14, the barcode attached to the side surface of the specimen container 51 is read by the barcode reader 14. In this case, the rotators 12a, 12b are first moved in the negative direction of the Y axis up to the position contacting the specimen container 51, and then rotated. The specimen container 51 rotates in the circumferential direction while being supported by the rotators 12a, 12b and the rotation supporter 13. The barcode is read by the barcode reader 14 when the barcode attached to the specimen container 51 is exactly facing the barcode reader 14.

The information read by the barcode reader 14 is transmitted to the information processing device 20 shown in FIG. 1. The information processing device 20 transmits the received barcode information, as well as the inquiry on the necessity of the examination on the relevant specimen and the examination items to the host computer 2. In response, the necessity of the examination and the examination items are transmitted from the host computer 2 to the information processing device 20. If the examination on the specimen is necessary, the execution of the examination and the measurement item are transmitted from the information processing device 20 to the measurement device 10. In response, the examination apparatus 10 performs the aspiration of the specimen by the nozzle 11 and performs the measurement of the specimen when the specimen container 51 accommodating the specimen reaches the aspirating position. This operation is performed on all specimen containers 51 of the rack 50.

When the rack 50 is moved to the most back side of the left bath region 31b by the transverse feeding mechanism section 36, the rack 50 is ultimately pushed in the negative direction of the Y axis by the rack pushing mechanism section 38, as shown in FIG. 4C. The rack 50 moved from the right bath region 31a to the left bath region 31b thus does not come to stationary at the most back side of the left bath region 31b, and hence the next rack 50 can be smoothly fed by the transverse feeding mechanism section 36.

Figure 5:
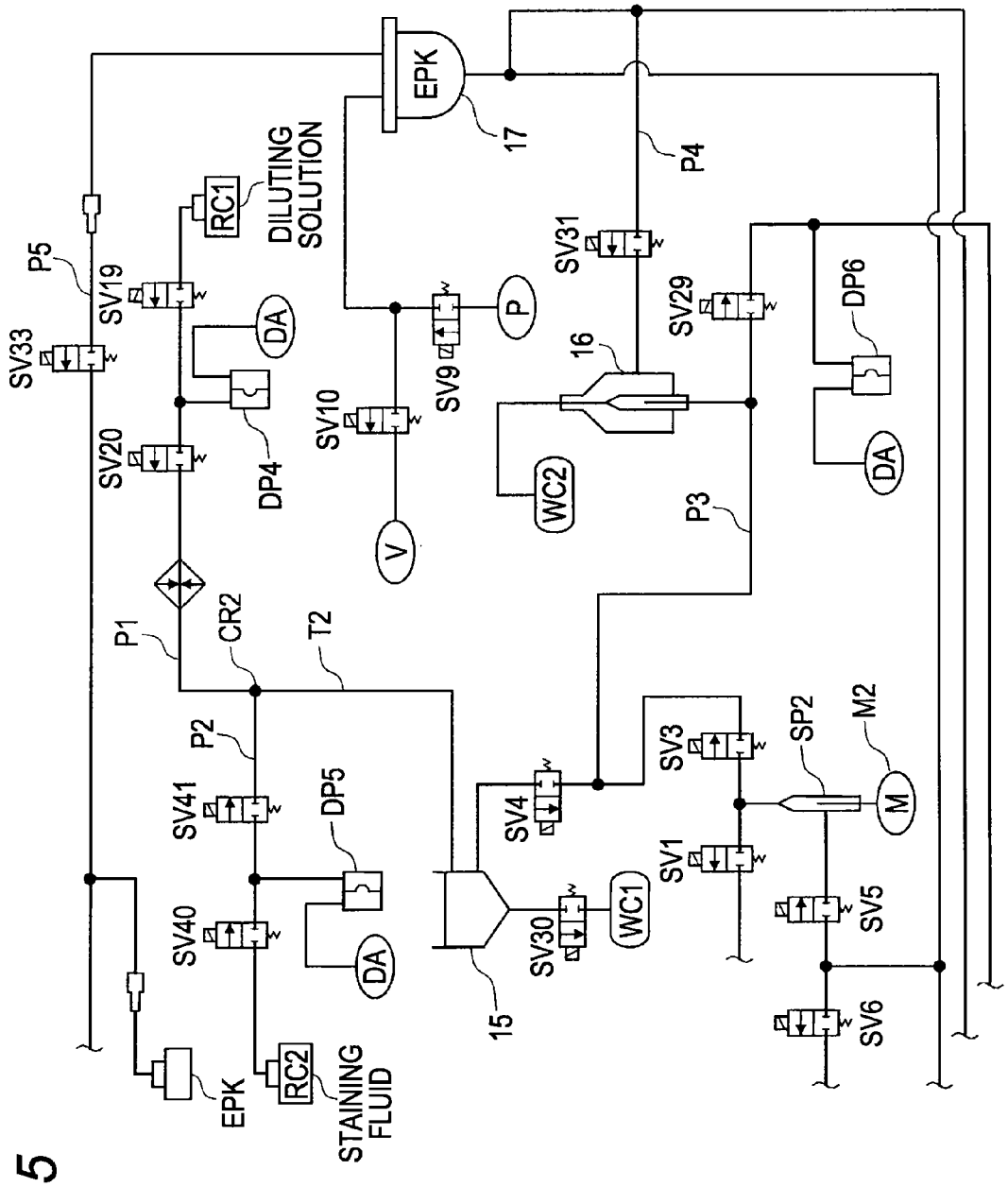
FIG. 5 is a fluid block diagram showing a configuration of a fluid unit according to the first embodiment.

FIG. 5 is a fluid circuit diagram showing a configuration of a fluid unit in the measurement device 10. As shown in the figure, the fluid unit includes a chamber, a plurality of electromagnetic valves, a diaphragm pump, and the like. The chamber 15 is used to prepare a measurement sample. The specimen aspirated by the nozzle 11 is supplied to the chamber 15.

The chamber 15 is connected to a reagent container RC1 for accommodating a diluting solution and a reagent container RC2 for accommodating a staining fluid by way of fluid communication paths P1, P2 such as a tube. Electromagnetic valves SV19, SV20 are arranged in the middle of the fluid communication path P1 connecting the chamber 15 and the reagent container RC1, and a diaphragm pump DP4 is arranged between the electromagnetic valves SV19, SV20. The diaphragm pump DP4 is connected to a positive pressure source P and a negative pressure source V (positive pressure source P and negative pressure source V configure a pneumatic source (see FIG. 6)) to positive pressure drive and negative pressure drive the diaphragm pump DP4. Electromagnetic valves SV40, SV41 are arranged in the middle of the fluid communication path P2 connecting the chamber 15 and the reagent container RC2, and a diaphragm pump DP5 is arranged between the electromagnetic valves SV40, SV41.

A control unit in the measurement device 10 controls the electromagnetic valves SV19, SV20, SV40, SV41, and the diaphragm pumps DP4, DP5 in the following manner to supply the diluting solution and the staining fluid to the chamber 15. The control unit will be described later with reference to FIG. 6.

First, the diaphragm pump DP4 is negative pressure driven with the electromagnetic valve SV19 arranged on the reagent container RC1 side than the diaphragm pump DP4 opened and the electromagnetic valve SV20 arranged on the chamber 15 side than the diaphragm pump DP4 closed to quantify and divide the diluting solution from the reagent container RC1. Thereafter, the diaphragm pump DP4 is positive pressure driven with the electromagnetic valve SV19 closed and the electromagnetic valve SV20 opened to supply the quantified diluting solution to the chamber 15.

Similarly, the diaphragm pump DP5 is negative pressure driven with the electromagnetic valve SV40 arranged on the reagent container RC2 side than the diaphragm pump DP5 opened and the electromagnetic valve SV41 arranged on the chamber 15 side than the diaphragm pump DP4 closed to quantify and divide the staining fluid from the reagent container RC2. Thereafter, the diaphragm pump DP5 is positive pressure driven with the electromagnetic valve SV40 closed and the electromagnetic valve SV41 opened to supply the quantified staining fluid to the chamber 15. The specimen and the reagent (diluting solution, staining fluid) are mixed in such a manner, and a sample of urine is prepared.

The chamber 15 is connected to a flow cell 16 by way of a fluid communication path P3 including a tube and an electromagnetic valve SV4. The fluid communication path P3 is branched in the middle, and electromagnetic valves SV1, SV3 are connected in series to the branched tip. A syringe pump P2 is arranged between the electromagnetic valves SV1, SV3. A stepping motor M2 is connected to the syringe pump P2, and the syringe pump P2 is driven by the operation of the stepping motor M2.

The fluid communication path P3 connecting the chamber 15 and the flow cell 16 is further branched, and an electromagnetic valve SV29 and a diaphragm pump DP6 are connected to the branched tip. When measuring urine with the flow cell 16, the diaphragm pump DP6 is negative pressure driven with the electromagnetic valves SV4, SV29 opened, and the sample is aspirated from the chamber 15, so that the sample is charged to the fluid communication path P3. The electromagnetic valves SV4, SV29 are closed after the charging of the sample is terminated. Thereafter, the electromagnetic valve SV3 is opened and the syringe pump P2 is drive, so that the charged sample is supplied to the flow cell 16.

As shown in FIG. 5, a sheath liquid chamber 17 is arranged in the fluid unit, and such a sheath liquid chamber 17 is connected to the flow cell 16 by way of a fluid communication path P4. The fluid communication path P4 includes an electromagnetic valve SV31. The sheath liquid chamber 17 is a chamber for storing the sheath liquid to be supplied to the flow cell 16, and is connected to a sheath liquid container EPK accommodating the sheath liquid by way of a fluid communication path P5 including an electromagnetic valve SV33. The diluting solution accommodated in the reagent container RC1 may be used as the sheath liquid.

The electromagnetic valve SV3 is opened to supply the sheath liquid to the sheath liquid chamber 17, and the sheath liquid is stored in the sheath liquid chamber 17 in advance before starting the measurement of urine. When starting the measurement of urine, the electromagnetic valve SV31 is opened to supply the sheath liquid stored in the sheath liquid chamber 17 to the flow cell 16 in synchronization with the supply of the sample to the flow cell 16.

The flow cell 16 is arranged inside an optical flow cytometer, and can measure urine through a flow cytometry method by semiconductor laser. In other words, the flow cell 16 is irradiated with laser light, and the forward scattered light, the lateral scattered light, and the lateral fluorescent are respectively detected by a photodetector. Particle data representing the pulse height value and the pulse width is generated by processing the signals (analog particle signals) from each photodetector.

Figure 6:
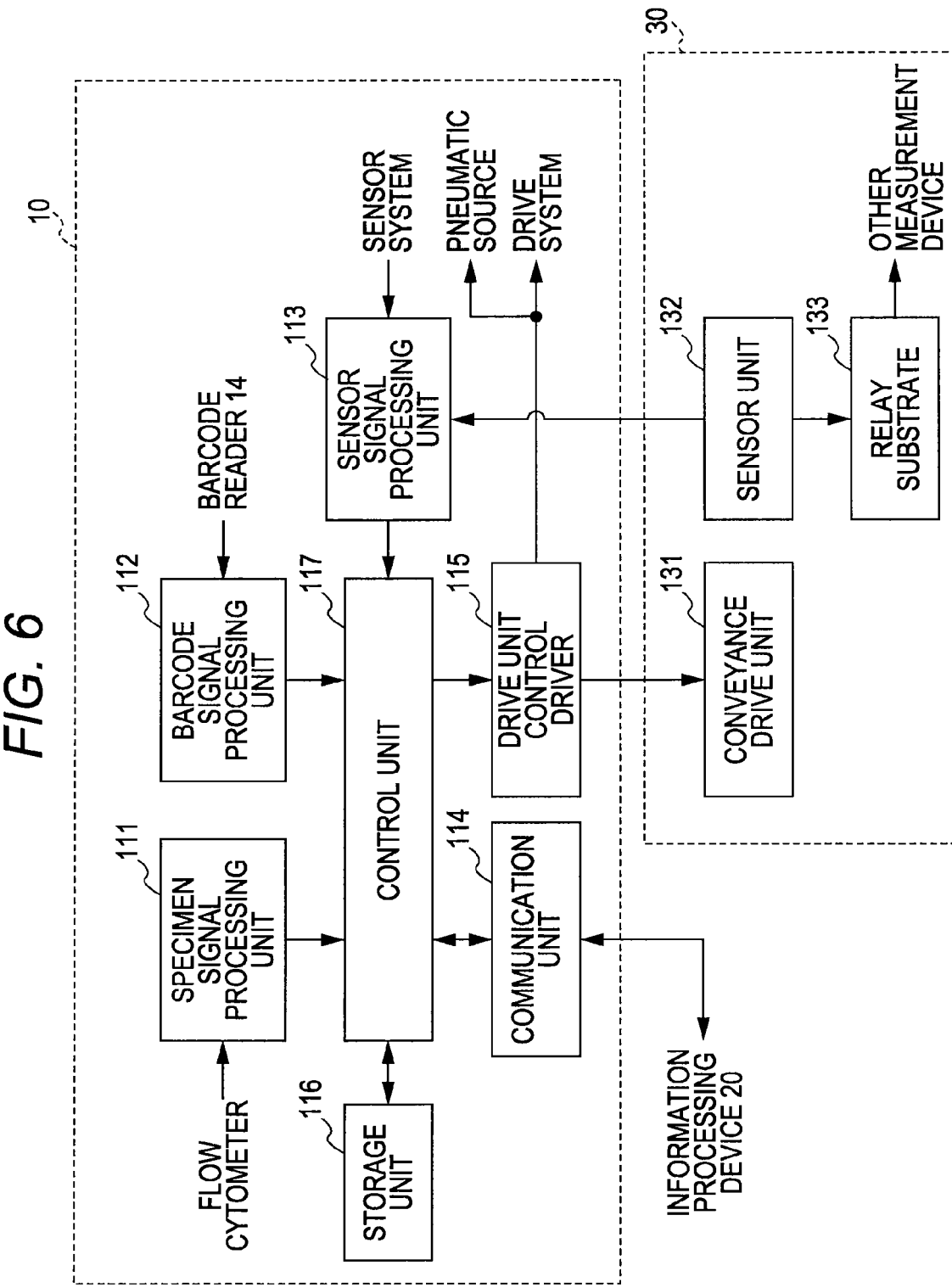
FIG. 6 is a circuit block diagram of the measurement device and the conveyance device according to the first embodiment.

FIG. 6 is a view showing a circuit configuration including the measurement device 10 and the conveyance device 30.

The measurement device 10 includes a specimen signal processing unit 111, a barcode signal processing unit 112, a sensor signal processing unit 113, a communication unit 114, a drive unit control driver 115, a storage unit 116, and a control unit 117. The conveyance device 30 includes a conveyance drive unit 131, a sensor unit 132, and a relay substrate 133.

The specimen signal processing unit 111 processes the signal detected by irradiating the flow cell 16 with laser light, and generates particle data. The generated particle data is once stored in the storage unit 116 through the control unit 117. The barcode signal processing unit 112 processes an output signal of the barcode reader 14, and generates barcode data. The sensor signal processing unit 113 processes outputs signals from a sensor system in the measurement device 10 and the sensor unit 132 in the conveyance device 30, and outputs the processing result to the control unit 117. The sensor system in the measurement device 10 includes a power switch of the measurement device 10.

The communication unit 114 processes the signal from the information processing device 20 and outputs to the control unit 117, and also processes the signal from the control unit 117 and outputs to the information processing device 20. The barcode data generated by the barcode signal processing unit 112 is transmitted from the communication unit 114 to the information processing device 20. In response thereto, the necessity of measurement and the measurement item of the specimen corresponding to the barcode data is transmitted from the information processing device 20 to the communication unit 114. After the measurement of the specimen is performed, the measurement result (particle data) is once stored in the storage unit 116, and then transmitted from the communication unit 114 to the information processing device 20.

The drive unit control driver 115 drives the pneumatic source and the drive system of the measurement device 10, and also drives the conveyance drive unit 131 of the conveyance device 30 based on the signal from the control unit 117. The pneumatic source of the measurement device 10 performs pressure supply to the nozzle 11 shown in FIG. 2, the diaphragm pump shown in FIG. 5, and the like. The drive system of the measurement device 10 includes a drive mechanism for driving the nozzle 11 and the rotators 12a, 12b shown in FIG. 2, and a drive mechanism for driving the electromagnetic valves, the stepping motor, and the like shown in FIG. 5.

The storage unit 116 stores the particle data generated by the specimen signal processing unit 111, the barcode data generated by the barcode signal processing unit 112, and the like. The storage unit 116 is also used as a work region of the control unit 117. The control unit 117 is configured by a ROM and a CPU, and controls each unit according to a control program stored in the ROM.

The conveyance drive unit 131 is driven based on a command from the drive unit control driver 115. The conveyance drive unit 131 includes the rack pushing mechanism section 33, the transverse feeding mechanism section 36, and the rack pushing mechanism section 38 shown in FIG. 3. The sensor unit 132 outputs the output signals from various types of sensors to the relay substrate 133, and the sensor signal processing unit 113 of the measurement device 10. The sensor unit 132 includes the sensor 32, the photo-interrupter 34, and the switches 35, 37 shown in FIG. 3. When another conveyance device is coupled to the conveyance device 30 and the rack 50 is conveyed to the measurement device 10 from another measurement device, the relay substrate 133 outputs the output signal from the sensor unit 132 to another measurement device.

In the information processing device 20, characteristic parameters (particle diameter, particle volume) are generated based on the measurement result (particle data) transmitted from the measurement device 10, and generation of particle size distribution diagram and scattergram, etc., are performed.

Figure 7:
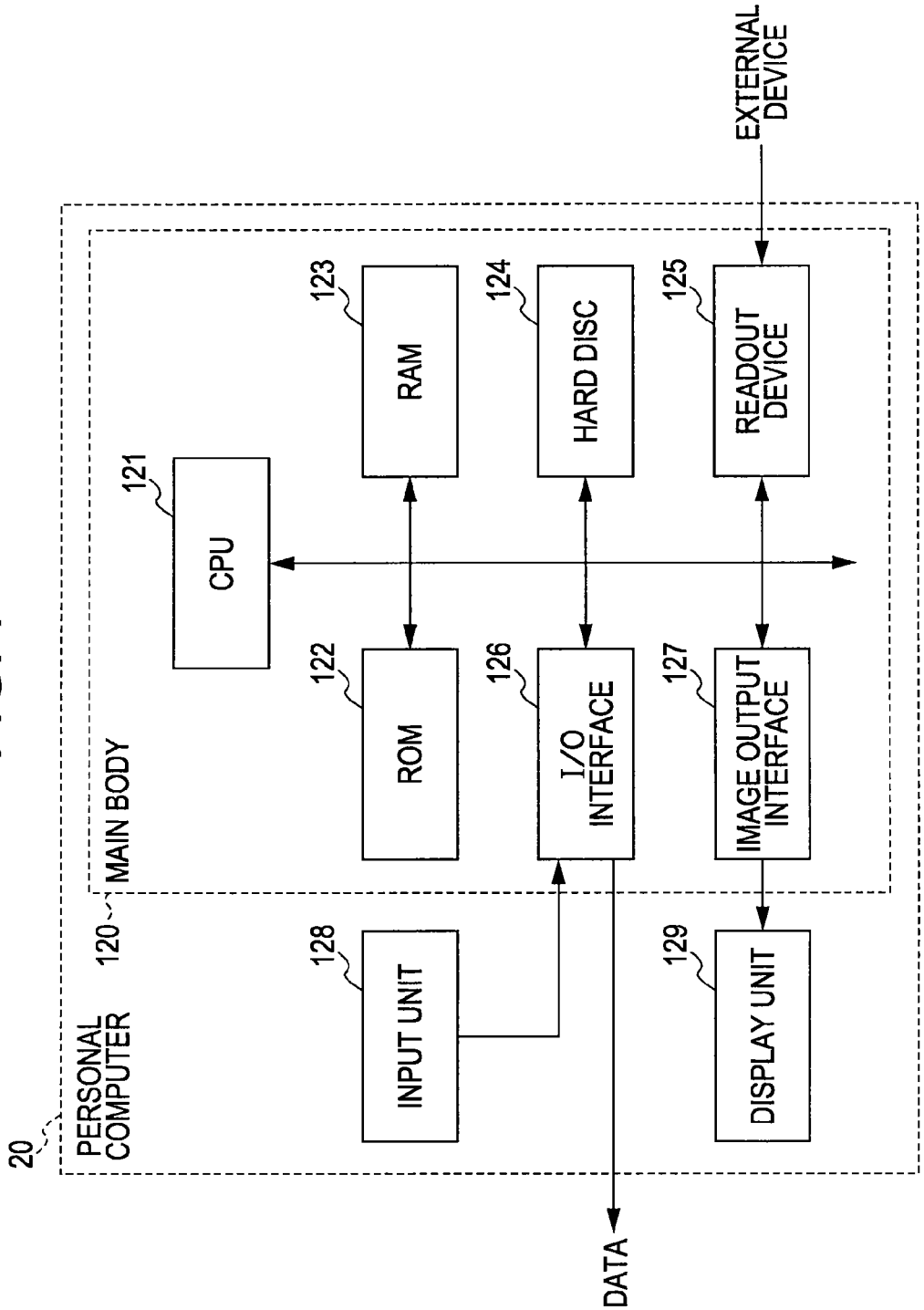
FIG. 7 is a block diagram showing a configuration of an information processing device according to the first embodiment.

FIG. 7 is a view showing a circuit configuration of the information processing device 20.

The information processing device 20 includes a personal computer, and is configured by a main body 120, an input unit 128, and a display unit 129. The main body 120 includes a CPU 121, a ROM 122, a RAM 123, a hard disc 124, a readout device 125, an I/O interface 126, and an image output interface 128.

The CP 121 executes a computer program stored in the ROM 122, and a computer program loaded in the RAM 122. The RAM 123 is used to readout the computer programs recorded in the ROM 122 and the hard disc 124. The RAM 123 is also used as a work region of the CPU 121 when executing such computer programs.

The hard disc 124 is installed with various computer programs to be executed by the CPU 121 such as the operating system and the application program, and the data used for the execution of the computer program. In other words, the hard disc 124 is installed with an operation program for performing the transmission of a measurement order (operation command) to the measurement device 10, the reception and the process of the measurement result measured by the measurement device 10, the display of the processed analysis result, and the like.

The readout device 125 is configured by a CD drive, a DVD drive, and the like, and can readout computer programs and data recorded in the recording medium. The I/O interface 126 is connected to the input unit 128 such as a mouse and a keyboard, where the user uses the input unit 128 to input data to the information processing device 20. As shown in FIG. 1, the data can be transmitted and received with respect to the measurement device 10 and the host computer 2 by the I/O interface 126.

The image output interface 127 is connected to the display unit 129 configured by a liquid crystal display and the like, and outputs a video signal corresponding to the image data to the display unit 129. The display unit 129 displays the image based on the input video signal.

Figure 8:
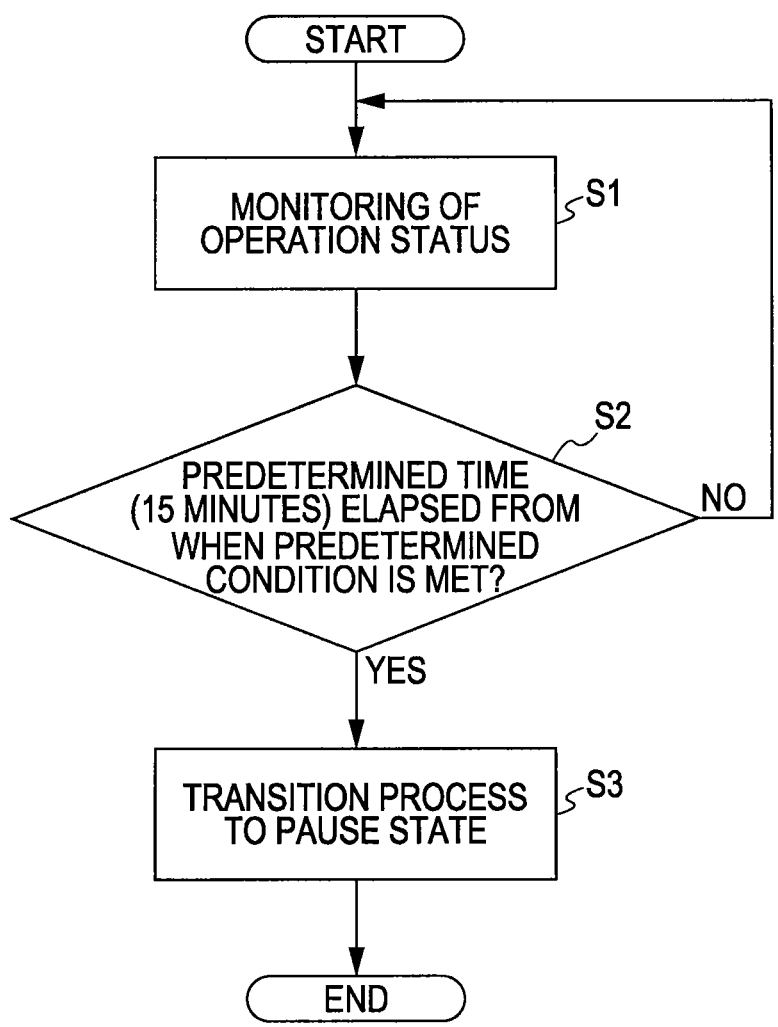
FIG. 8 is a flowchart showing a transition process to a pause state according to the first embodiment.

FIG. 8 is a view showing the processing flow of transition to the pause state according to the present embodiment.

In S1, the operation status of the measurement device 10 and the conveyance device 30 is monitored by the control unit 117 shown in FIG. 6.

In S2, whether or not a predetermined time (15 minutes) has elapsed from when a predetermined condition is met in the monitoring of the operation status. When determined that the predetermined time (15 minutes) has elapsed (S2: YES), the process proceeds to S3. When determined that the predetermined time (15 minutes) has not elapsed (S2: NO), the process returns to S1 and the monitoring of the operation status is continued.

The predetermined condition is a state in which the rack 50 is not detected by the sensor 32, and the switches 35, 37. The setting of such a predetermined condition can be changed by the user according to the usage mode. For instance, the predetermined condition may be a state in which the rack 50 is not detected by one of the sensor 32, or the switches 35, 37. The predetermined time is 15 minutes herein, but may be changed by the user according to the usage mode. This change is made from the input unit 128 of the information processing device 20.

In S3, the transition process is performed such that the measurement device 10 is in the pause state. The pause state is a state in which the power supply to the pneumatic source shown in FIG. 6 is stopped. Specifically, when the transition process to the pause state starts, the closing of the electromagnetic valve of the fluid unit, and the like are carried out such that the sample, etc., do not mix, and then the power supply to the pneumatic source is stopped.

The processing flow when the pause state is released and the measurement is resumed will be described below with reference to FIG. 9 to FIG. 12.

Figure 9:
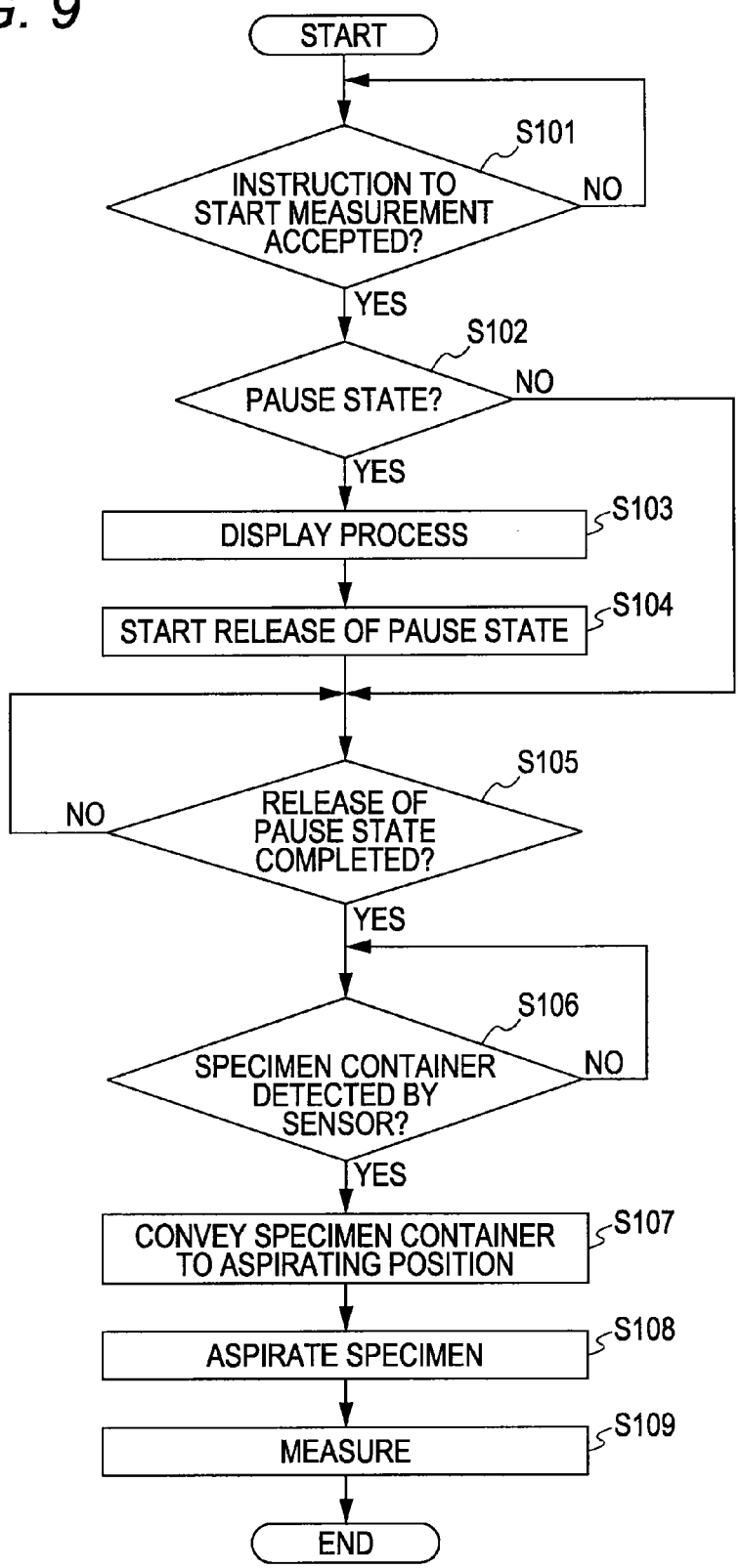
FIG. 9 is a flowchart showing a resuming process 1 according to the first embodiment.

FIG. 9 is a view showing the processing flow of the resuming process 1.

The control unit 117 determines whether or not the user made an instruction to start the measurement to the information processing device 20 by the signal from the information processing device 20 (S101). The start of measurement is instructed when the user selects the start button displayed on the display unit 129 of the information processing device 20. When accepting the instruction to start the measurement (S101: YES), the control unit 117 determines whether or not the current state is the pause state (S102). The control unit 117 performs the process of S103 if the current state is the pause state (S102: YES), and the control unit 117 performs the process of S105 if the current state is not the pause state (S102: NO).

In S103, the control unit 117 transmits a signal for causing the display unit 129 of the information processing device 20 to make a display of a notification "pause state is automatically released, and aspiration task of the specimen is started" to the information processing device 20 through the communication unit 114. In response, the information processing device 20 makes such a display on the display unit 129. Even users who are not familiar with the operation of the device thus can recognize that the aspirating operation is automatically started after the release of the pause state, and that the user can move away from the device.

The control unit 117 starts the release of the pause state in the following S104. The preparation operation such as the drive of the pneumatic source, and the like is then carried out. In S105, whether or not the release of the pause state is completed is determined.

When determining that the release of the pause state is completed (S105: YES), the control unit 117 determines whether or not the specimen container 51 (rack 50) exists at the receiving position by the signal from the sensor 32 of the conveyance device 30 (S106). If the specimen container 51 is set at the receiving position (S106: YES), the conveyance of the rack 50 is executed so that the specimen in the specimen container 51 can be aspirated (S107). In other words, the control unit 117 controls the conveyance drive unit 131 of the conveyance device 30 through the drive unit control driver 115 based on the signal from the sensor unit 132 of the conveyance device 30. The rack 50 is thereby moved, and the specimen container 51 is positioned at the aspirating position.

Thereafter, the control unit 117 aspirates the specimen from the specimen container 51 conveyed to the aspirating position through the drive unit control driver 115, and supplies the aspirated specimen to the chamber 15 of the fluid unit (FIG. 5) (S108). Subsequently, the control unit 117 performs the measurement of the specimen using the flow cytometer, and processes the measurement result in the specimen signal processing unit 111 to generate the particle data (S109). The control unit 117 then transmits the generated particle data to the information processing device 20 through the communication unit 114.

Figure 10:
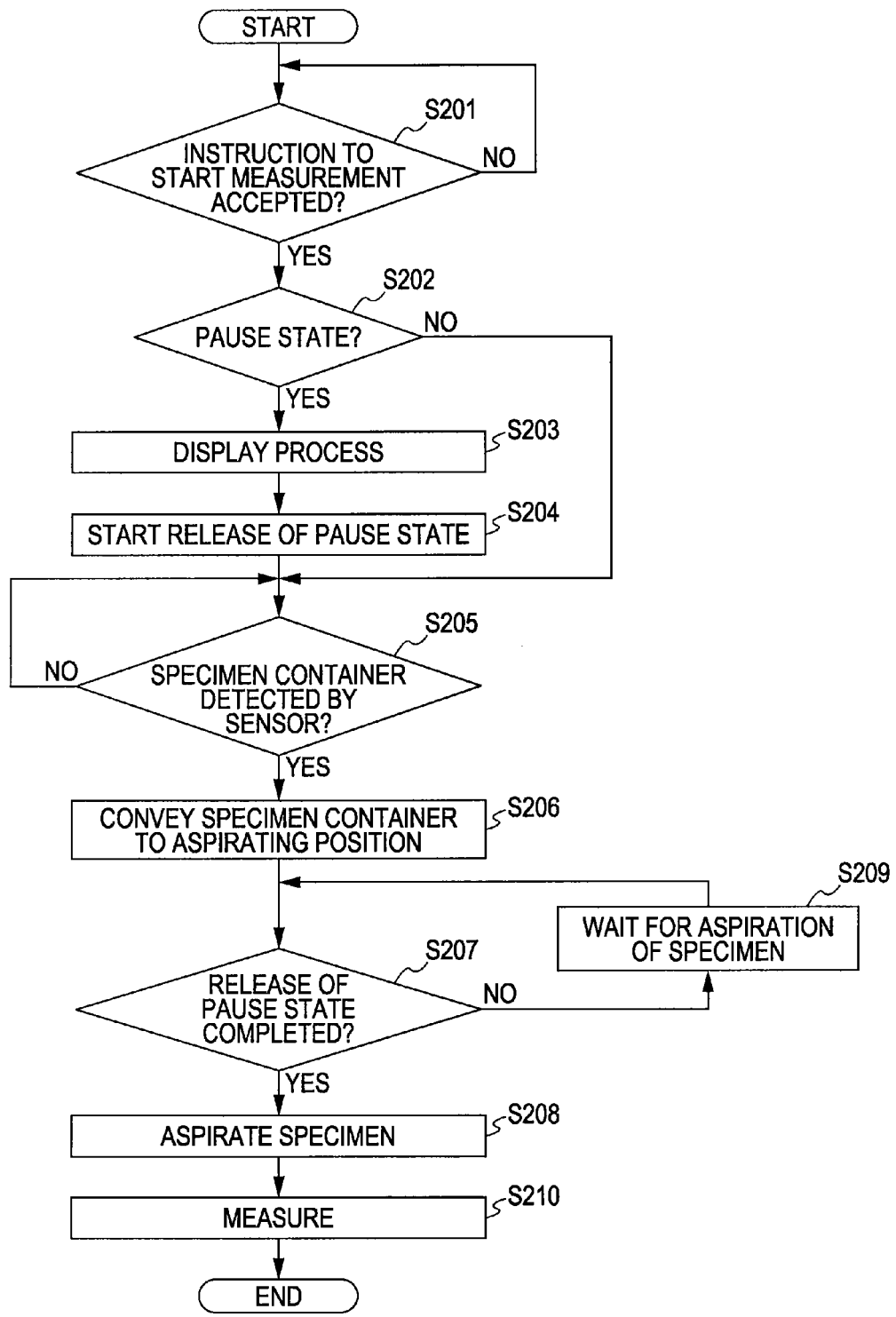
FIG. 10 is a flowchart showing a resuming process 2 according to the first embodiment.

FIG. 10 is a view showing the processing flow of the resuming process 2 in which one part of the processing flow of the resuming process 1 is changed. S201 to S204 in the figure are the same as S101 to S104 of the resuming process 1 shown in FIG. 9, and thus 5205 and the steps thereafter will be described.

The control unit 117 determines whether or not the specimen container 51 (rack 50) exists at the receiving position by the signal from the sensor 32 of the conveyance device 30 (S205). If the specimen container 51 is set at the receiving position (S205: YES), the conveyance of the rack 50 is executed so that the specimen in the specimen container 51 can be aspirated (S206). In other words, the control unit 117 controls the conveyance drive unit 131 of the conveyance device 30 through the drive unit control driver 115 based on the signal from the sensor unit 132 of the conveyance device 30. The rack 50 is thereby moved, and the specimen container 51 is positioned at the aspirating position.

Thereafter, the control unit 117 determines whether or not the release of the pause state is completed (S207). The control unit 117 performs the process of S208 when determining that the release of the pause state is completed (S207: YES), and the control unit 117 performs the process of S209 when determining that the release of the pause state is not completed (S207: NO).

In S209, the specimen container 51 is at the aspirating position, but the specimen cannot be immediately aspirated from the specimen container 51 since the release of the pause state is not completed. The control unit 117 thus waits for the aspiration of the specimen.

In S208, the control unit 117 aspirates the specimen from the specimen container 51 conveyed to the aspirating position through the drive unit control driver 115, and supplies the aspirated specimen to the chamber 15 of the fluid unit (FIG. 5). Subsequently, the control unit 117 performs the measurement of the specimen using the flow cytometer, and processes the measurement result in the specimen signal processing unit 111 to generate the particle data (S210). The control unit 117 then transmits the generated particle data to the information processing device 20 through the communication unit 114.

Therefore, according to the resuming process 2, the aspiration of the specimen can be immediately started after the pause state is released since the specimen container 51 is conveyed to the aspirating position before the completion of the pause state. Therefore, the aspiration of the specimen can be started earlier in the resuming process 2 than in the resuming process 1. Furthermore, according to the resuming process 2, occurrence of drawbacks that occur when the specimen is aspirated before the release of the pause state is completed can be, reliably prevented since the aspiration of the specimen is waited until the release of the pause state is completed.

Figure 11:
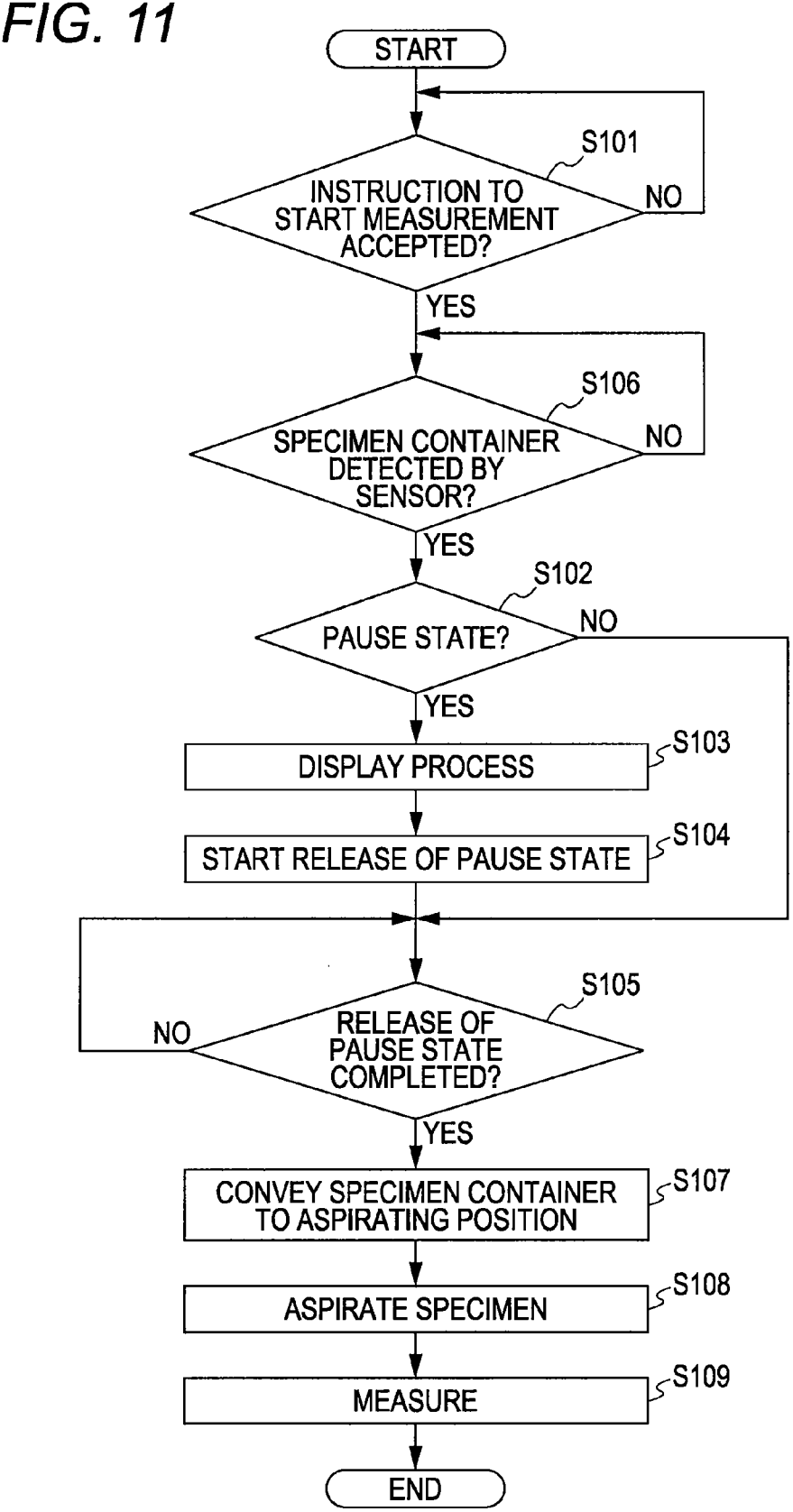
FIG. 11 is a flowchart showing a resuming process 3 according to the first embodiment.

FIG. 11 is a view showing the processing flow of the resuming process 3.

The resuming process 3 is the processing flow when S106, which is between S105 and S107 in the processing flow of the resuming process 1 shown in FIG. 9, is between S101 and S102.

In this case, when accepting the instruction to start the measurement (S101: YES), the control unit 117 determines whether or not the specimen container 51 (rack 50) exists at the receiving position (S106) by the signal from the sensor 32 of the conveyance device 30 before determining whether or not the current state is the pause state (S102). Thus, even if the control unit 117 accepts the instruction to start the measurement, the pause state will not be released unless the specimen container 51 is set at the receiving position.

Accordingly, the pause state is avoided from being release in a state the specimen container 51 (rack 50) is not set at the receiving position, and unnecessary power is prevented from being consumed.

Figure 12:
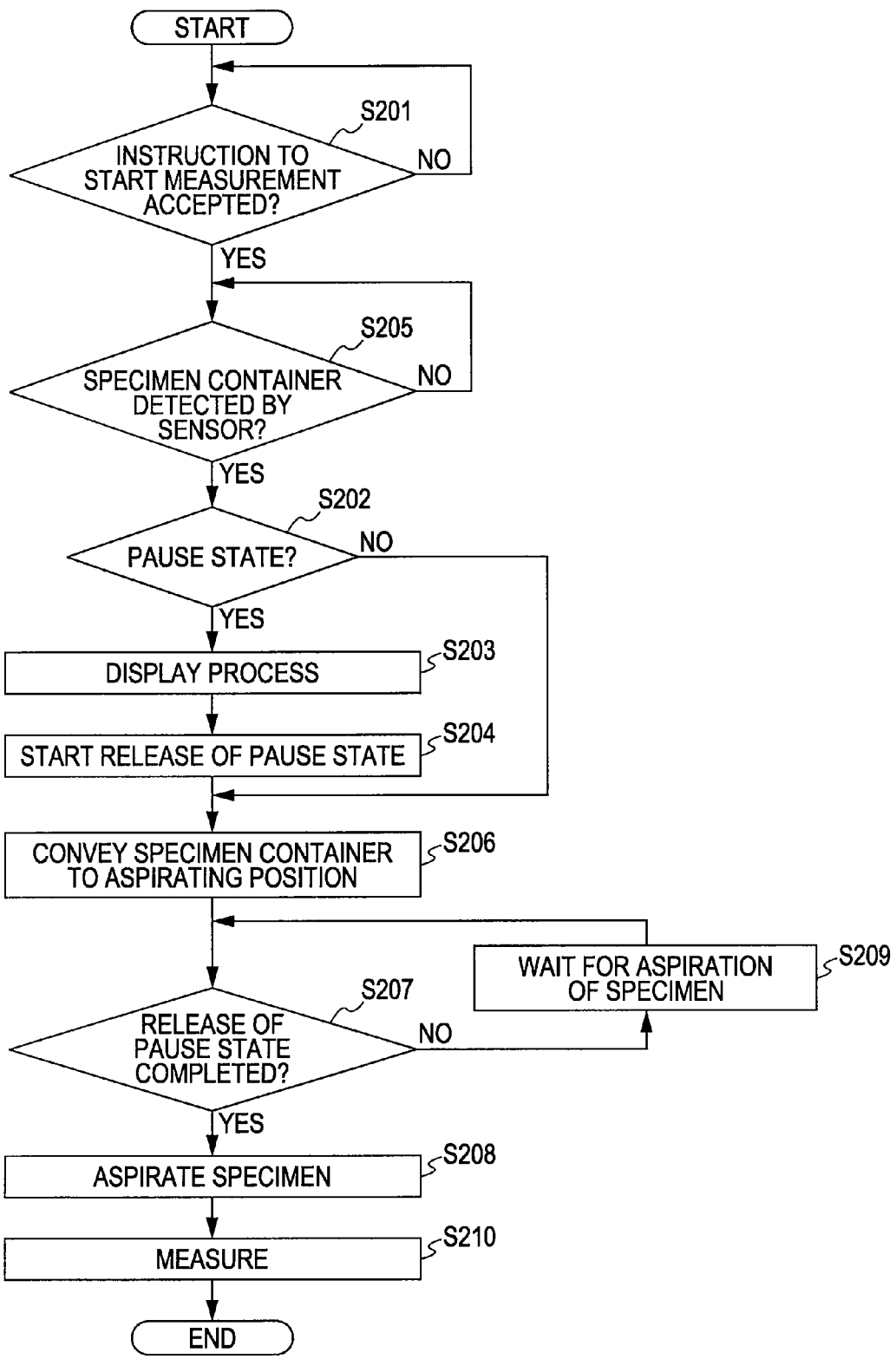
FIG. 12 is a flowchart showing a resuming process 4 according to the first embodiment.

FIG. 12 is a view showing the processing flow of the resuming process 4.

The resuming process 4 is the processing flow when S205 between S204 and S206 in the resuming process 2 shown in FIG. 10 is between S201 and S202.

In this case, when accepting the instruction to start the measurement (S201: YES), the control unit 117 determines whether or not the specimen container 51 (rack 50) exists at the receiving position (S205) by the signal from the sensor 32 of the conveyance device 30 before determining whether or not the current state is the pause state (S202). Thus, even if the control unit 117 accepts the instruction to start the measurement, the pause state will not be released unless the specimen container 51 is set at the receiving position.

Similar to the resuming process 3, the pause state is avoided from being released in a state the specimen container 51 (rack 50) is not set at the receiving position, and the unnecessary power can be prevented from being consumed.

According to the present embodiment, the measurement device 10 enters the pause state when a predetermined time has elapsed after the measurement device is in the non-operation state. The unnecessary power supply is reduced at the pneumatic source of large power consumption, and the power consumption of the specimen examination apparatus can be suppressed low. When the measurement device 10 enters the pause state, the noise caused by the drive of the pneumatic source can be reduced.

According to the present embodiment, when accepting the instruction to start the measurement, the control unit 117 releases the pause state and executes the measurement operation. The user does not need to wait until the specimen examination apparatus undergoes transition from the pause state to the measurable state, and can perform the measurement on the specimen by simply instructing start.

According to the resuming processes 3, 4, the power consumption can be reduced, but on the contrary, the pause state is released after the specimen container 51 (rack 50) is set at the receiving position, and thus time is required until the specimen examination starts. In the resuming processes 1, 2, on the other hand, the pause state is already released before the specimen container 51 (rack 50) is set at the receiving position, and thus the specimen examination can be rapidly carried out after the specimen container 51 (rack 50) is set at the receiving position. Thus, the resuming processes 1, 2 are preferable when prioritizing urgency such as in time of emergency. Therefore, the mode of the resuming process may be switched between the resuming processes 1, 2 and the resuming processes 2, 3. The user may set to the power consumption saving mode (resuming processes 3, 4) in the time zone in which the patients are few, and switch to the emergency mode (resuming processes 1, 2) when notification or acceptation of emergency is made to prepare for rapid response.

The specimen examination apparatus of the first embodiment is configured to release the pause state and measure the specimen when accepting the instruction to start the measurement with respect to the information processing device 20, but to release the pause state and measure the specimen when accepting the instruction to start the measurement by other means.

Figure 13:
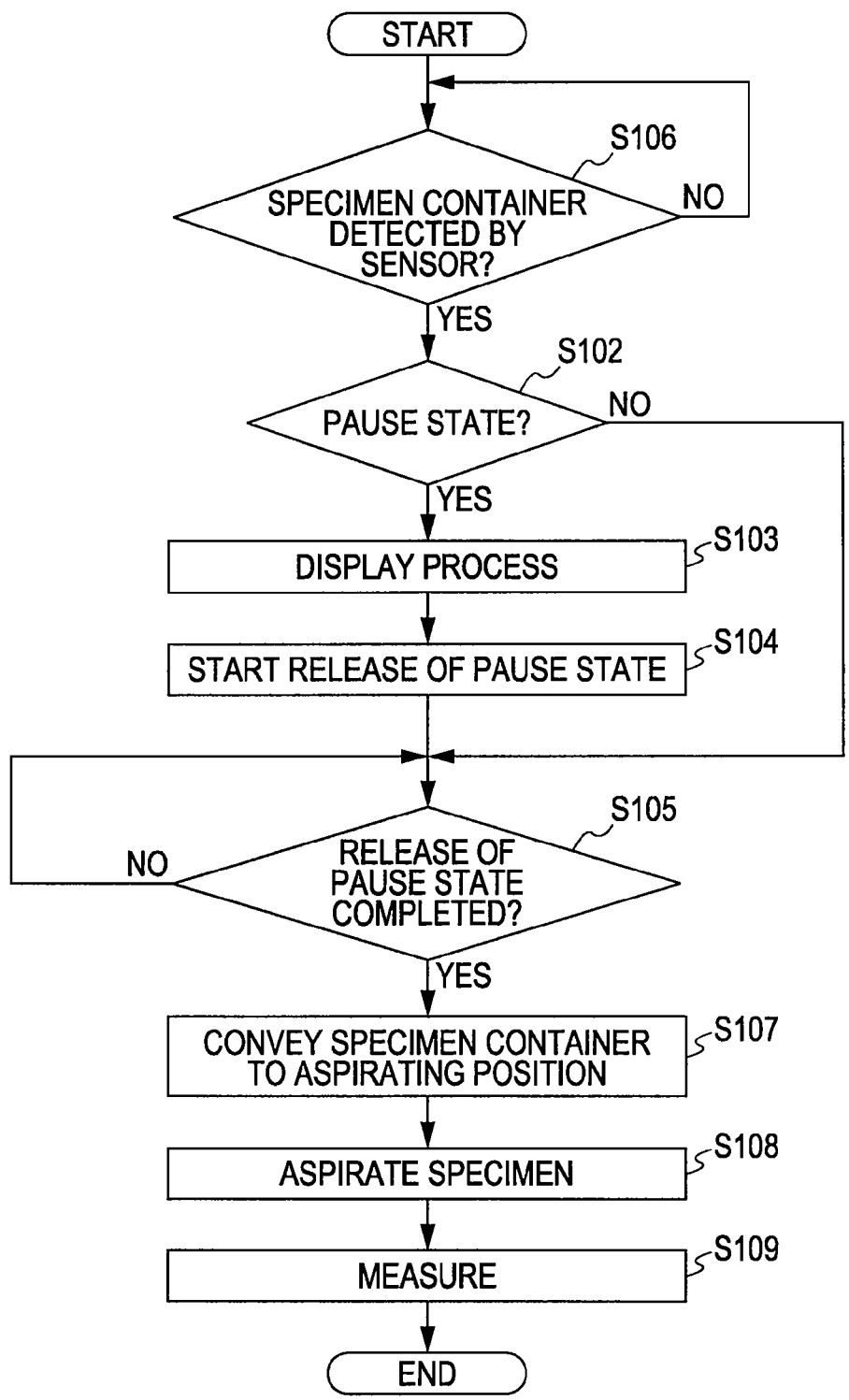
FIG. 13 is a flowchart showing a resuming process 5 in which the resuming process 3 is changed.

FIG. 13 is a view showing the processing flow of the resuming process 5.

The resuming process 5 is the flow when S101 is deleted in the processing flow of the resuming process 3 shown in FIG. 11.

In this case, the control unit 117 determines whether or not the specimen container 51 (rack 50) exists at the receiving position (S106) by the signal from the sensor 32 of the conveyance device 30. When determining that the specimen container 51 (rack 50) exists (S106: YES), the control unit 117 performs the processes after S102, and measures the specimen in S109. The processes after S102 are similar to the resuming process 3, and thus the description thereof will be omitted.

In the resuming process 5, when the existence of the specimen container 51 (rack 50) is detected, that is, when the instruction to start the measurement is accepted by the detection of the existence of the specimen container 51 (rack 50), the pause state is released and the specimen is measured.

Figure 14:
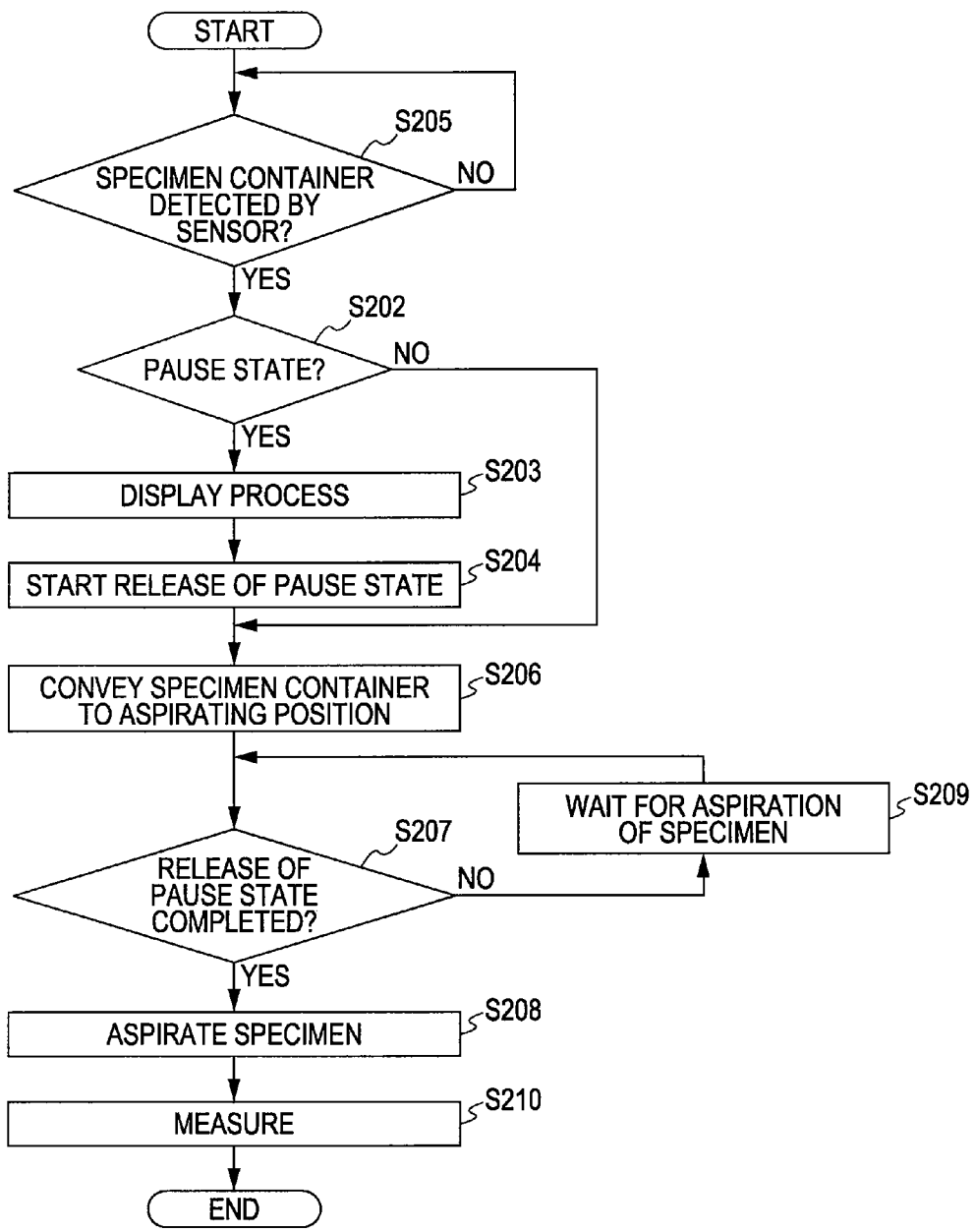
FIG. 14 is a flowchart showing a resuming process 6 in which the resuming process 4 is changed.

FIG. 14 is a view showing the processing flow of the resuming process 6.

The resuming process 6 is the flow when S201 is deleted in the processing flow of the resuming process 4 shown in FIG. 12.

In this case, the control unit 117 determines whether or not the specimen container 51 (rack 50) exists at the receiving position (S205) by the signal from the sensor 32 of the conveyance device 30. When determining that the specimen container 51 (rack 50) exists (S205: YES), the control unit 117 performs the processes after S202, and measures the specimen in S209. The processes after S202 are similar to the resuming process 4, and thus the description thereof will be omitted.

In the resuming process 6, when the existence of the specimen container 51 (rack 50) is detected, that is, when the instruction to start the measurement is accepted by the detection of the existence of the specimen container 51 (rack 50), the pause state is released and the specimen is measured.

According to the resuming process 6, the specimen container 51 is conveyed to the aspirating position without waiting for the completion of the pause state, and thus the aspiration of the specimen can be started immediately after the pause state is released. In the resuming process 6, the measurement and the analysis of the specimen can be more rapidly executed compared to the resuming process 5. According to the resuming process 6, the aspiration of the specimen is waited until the release of the pause state is released, and thus the occurrence of drawbacks that occur when the specimen is aspirated before the release of the pause state is completed can be reliably prevented.

Figure 15:
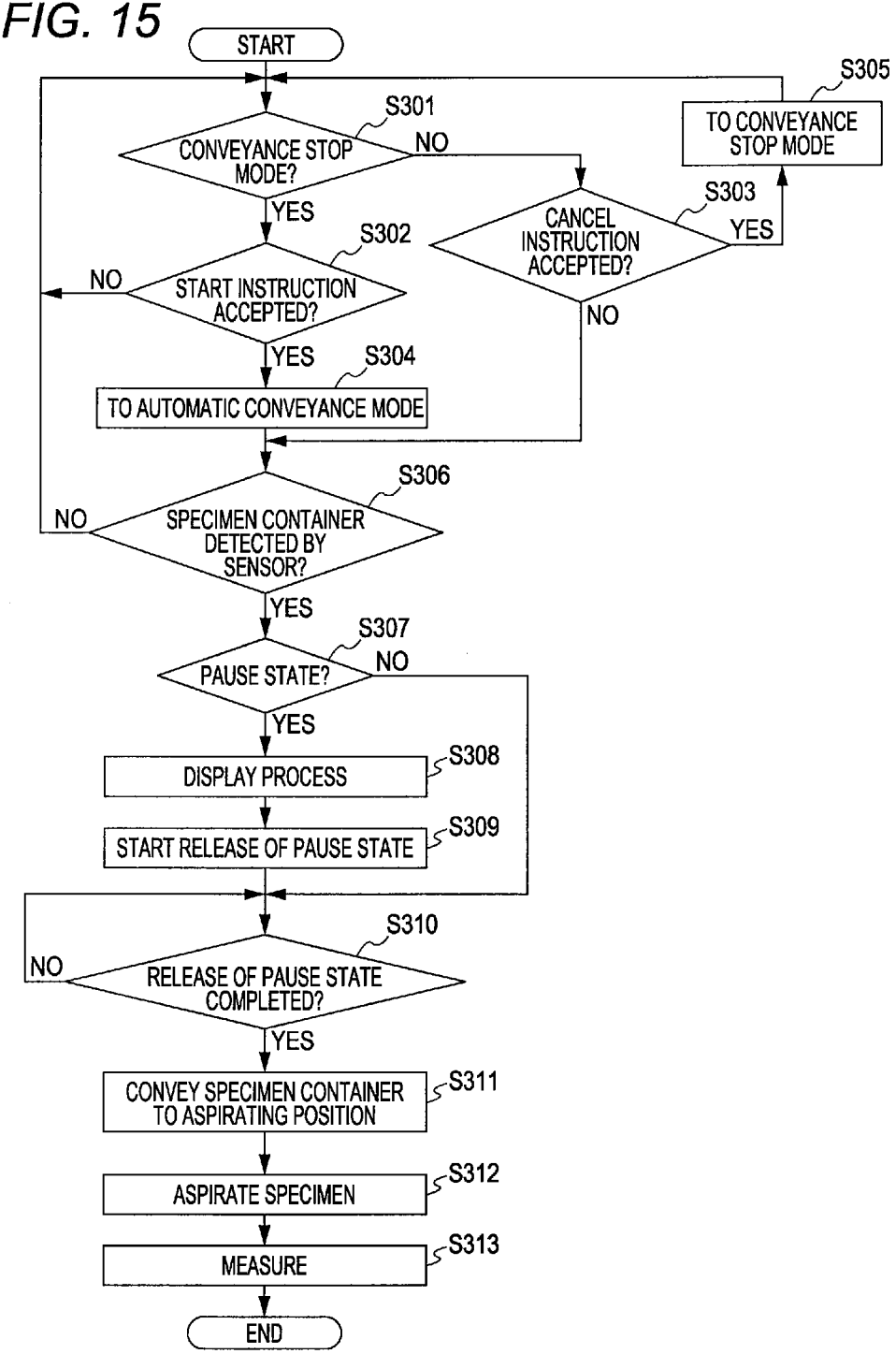
FIG. 15 is a flowchart showing a resuming process 7 according to the first embodiment.

FIG. 15 is a view showing the processing flow of the resuming process 7.

The resuming process 7 has the processing mode (hereinafter referred to as "automatic conveyance mode") in which the pause state is automatically released and the aspiration of the specimen is started when the specimen container 51 is detected by the sensor 32, and the processing mode (hereinafter referred to as "conveyance stop mode") in which the pause state is not automatically released and the aspiration of the specimen is not started when the specimen container 51 is detected by the sensor 32. Such processing modes can be set through the information processing device 20.

In S301, the control unit 117 determines whether or not the current processing mode is the conveyance stop mode. If in the conveyance stop mode (S301: YES), the control unit 117 determines whether or not the measurement device 10 accepted the instruction to start (S302). When the measurement device 10 accepts the instruction to start from the information processing device 20 when the user operates the information processing device 20 (S302: YES), the control unit 117 changes the processing mode from the conveyance stop mode to the automatic conveyance mode (S304).

In S301, when determined that the current processing mode is the automatic conveyance mode (S301: NO), the control unit 117 determines whether or not the measurement device 10 accepted the instruction to cancel (S303). When the measurement device 10 accepts the instruction to cancel from the information processing device 20 when the user operates the information processing device 20 (S303: YES), the control unit 117 changes the processing mode from the automatic conveyance mode to the conveyance stop mode (S305).

When the specimen container 51 is detected by the sensor 32 (S306: YES) when the processing mode is in the automatic conveyance mode (S303: No, S304), the control unit 117 proceeds to S307, and releases the pause state. S307 to S313 are the processing flow similar to S101 to S108 of the resuming process 5 shown in FIG. 13, and thus the description thereof will be omitted.

The acceptance of the cancel instruction of S303 is set so as to be executable even during the execution of one of the processing flows of S301 to S313. In other words, the current processing mode can be immediately changed to the conveyance stop mode if the cancel instruction is accepted even during the processing. In this case, the specimen 51 already being executed with the processing is executed until the final processing flow (S313) without delay.

According to the resuming process 3, when the current processing mode is the conveyance stop mode, the processes after S306 are not performed unless the instruction to start is accepted. Therefore, the measurement device 10 is prevented from being released from the pause state unexpectedly during the adjustment work of the measurement unit. In the resuming process 3, the user can arbitrarily switch the processing mode to the automatic conveyance mode or the conveyance stop mode by giving the start instruction or the cancel instruction to the measurement device 10. In particular, since the processing mode can be automatically switched to the conveyance stop mode by giving the cancel instruction in the resuming process 3, the pause state is avoided from being released although the user does not have the intention of processing the specimen, and the wasteful power is avoided from being consumed.

If the processing mode is in the conveyance stop mode, the detection by the sensor 32 may be completely stopped. The specimen container 51 is thus not detected by the sensor 32 even if the specimen container 51 is at the receiving position, and hence the wasteful detection operation in the sensor 32 can be suppressed.

Figure 16:
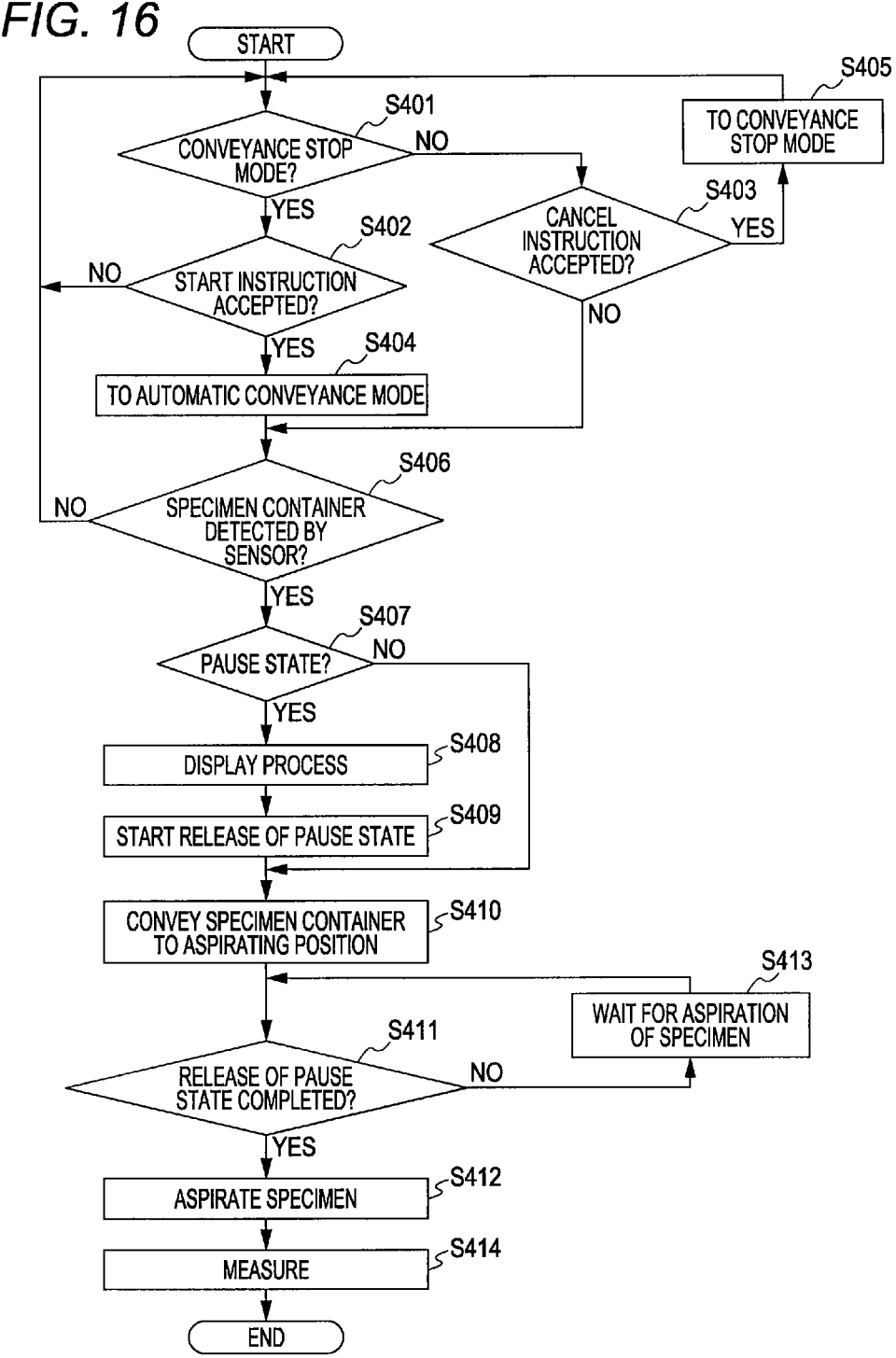
FIG. 16 is a flowchart showing a resuming process 8 according to the first embodiment.

FIG. 16 is a view showing the processing flow of the resuming process 8 in which one part of the resuming process is changed. S406 to S414 and S401 to S406 in the figure are the same as S202 to S210 of the resuming process 6 shown in FIGS. 14, and S301 to S306 of the resuming process 7 shown in FIG. 15. Thus, the effects of the resuming process 6 can be obtained in addition to the effects by the resuming process 7.

According to the present embodiment, the measurement device 10 enters the pause state when a predetermined time has elapsed after the measurement device is in the non-operation state. The unnecessary power supply is reduced at the pneumatic source with large power consumption, and the power consumption of the specimen examination apparatus can be suppressed low. When the measurement device 10 enters the pause state, the noise caused by the drive of the pneumatic source can be reduced.

Furthermore, according to the present embodiment, when the sensor 32 detects the specimen container 51 at the receiving position, the pause state of the measurement device 10 and the conveyance device 30 is released, the specimen container 51 is conveyed to the aspirating position, and thus the measurement is started. The user does not need to again instruct the start of examination after the pause state is released, and hence the operation steps can be simplified.

According to the present embodiment, the processing mode is set to either the automatic conveyance mode or the conveyance stop mode. The measurement unit is prevented from being released from the pause state unexpectedly when the processing mode is in the conveyance stop mode.

According to the present embodiment, the start instruction and the cancel instruction can be given to the measurement device 30 through the information processing device 20. The processing mode can be thus changed to the conveyance stop mode in the automatic conveyance mode, and the processing mode can be changed to the automatic conveyance mode in the conveyance stop mode.

The specimen examination apparatus of the first embodiment is configured to automatically release the pause state and measure the specimen when the specimen container is detected by the sensor, but may be configured to disable the start button, which is disabled in the pause state, when the specimen container is detected by the sensor, and release the pause state and measure the specimen when the instruction to start the measurement is accepted.

Figure 17:
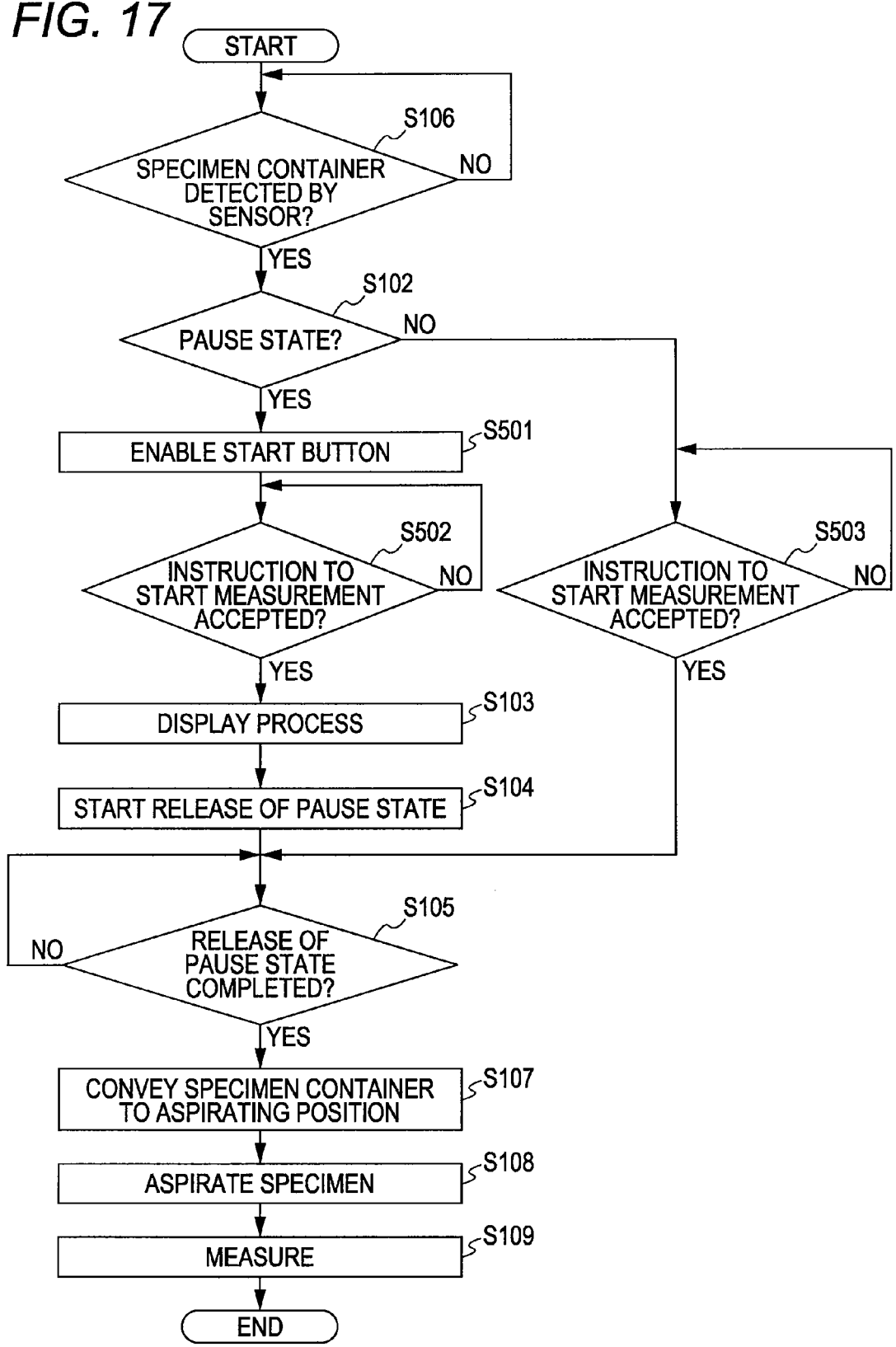
FIG. 17 is a flowchart showing a resuming process 9 in which the resuming process 1 is deformed.

FIG. 17 is a view showing the processing flow of the resuming process 9.

The resuming process 9 is the flow when S501 and S502 are arranged between S102 and S103 in the processing flow of the resuming process 1 shown in FIGS. 13, and S503 is arranged as in the figure.

In this case, when the specimen container is detected by the sensor (S106: YES) and determination is made as pause state (S102: YES), the control unit 117 activates the start button displayed on a display unit 129 of the information processing device 20 (S501). Specifically, when the specimen examination apparatus 1 is in the pause state, the CPU 121 of the information processing device 20 does not transmit any signal to the control unit 117 of the measurement device 10 and disables the start button even when receiving the selection of the displayed start button from the user. The CPU 121 of the information processing device 20 transmits a signal indicating the instruction to start the measurement to the control unit 117 when accepting the selection of the displayed start button from the user through the enabling process of S501. The control unit 117 then determines whether or not the user made an instruction to start the measurement with respect to the information processing device 20 by the signal from the information processing device 20 (S502). When accepting the instruction to start the measurement (S502: YES), the control unit 117 executes the process of S103. The processes after S103 are similar to the resuming process 1, and thus the description thereof will be omitted. If determined as not the pause state in S102 (S102: NO), the control unit 117 determines whether or not the user made an instruction to start the measurement with respect to the information processing device 20 (S503). In this case, the device is not in the pause state, and thus the start button is in the activated state. The control unit 117 executes the processes after S105 when accepting the instruction to start the measurement (S503: YES).

In addition, the instruction to start the measurement may be accepted through reception of the signal from the higher-order computer. The signal from the higher-order computer includes a measurement order containing information indicating that the measurement is necessary, and information indicating the measurement item that requires measurement.

The instruction to start the measurement may be accepted when the barcode reader reads the barcode given to the specimen container.

2. Second Embodiment

The specimen examination apparatus according to the second embodiment will be described with reference to the drawings. In the present embodiment, the specimen rack is automatically set in the specimen examination apparatus. In the present embodiment, the description on the configurations shown in the first embodiment will be omitted.

Figure 18:
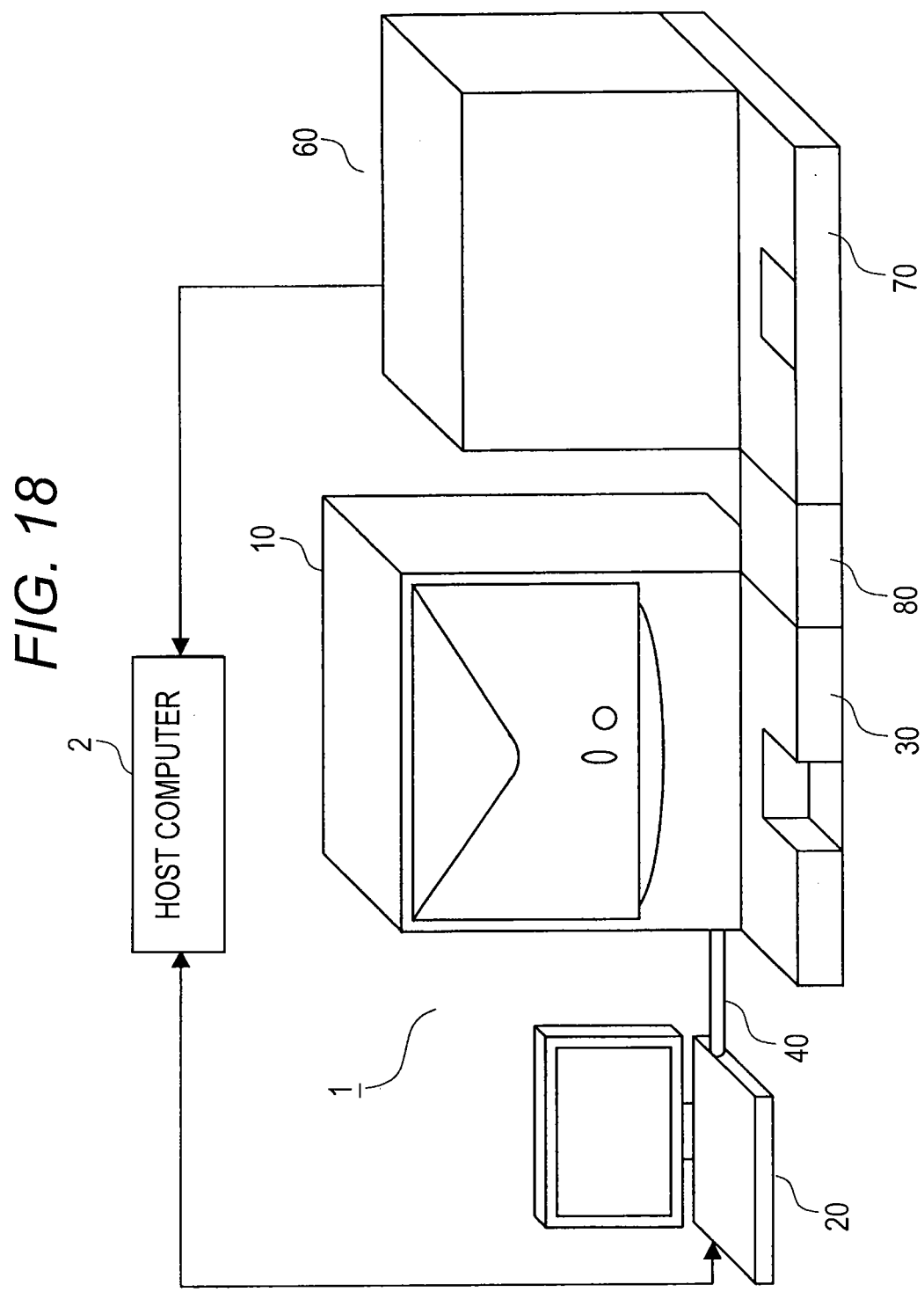
FIG. 18 is a view showing a configuration of a specimen examination system according to a second embodiment.

FIG. 18 is a view showing the configuration of the entire system including the specimen examination apparatus 1. In addition to the specimen examination apparatus 1 according to the first embodiment, the examination system according to the present embodiment includes another specimen examination apparatus including a measurement device 60 and a conveyance device 70.

The measurement device 60 aspirates the specimen accommodated in the specimen container, and performs the measurement through qualitative analysis (examinations on urinary protein, glucose in urine, etc.) on the aspirated specimen. The measurement result of each specimen is transmitted to the host computer 2. The conveyance device 70 conveys the rack, and installs each specimen container held at the rack at the position where aspiration can be carried out by the measurement device 60. Furthermore, when the aspiration of the specimen with respect to all specimen containers held at the rack is terminated, the rack is conveyed to the discharging position. The rack discharged at the discharging position is conveyed to the receiving position of the conveyance device 30 through a connection conveyance device 80.

The control unit 117 of the specimen examination apparatus 1 executes the resuming process 5 or 6. In other words, when the rack is conveyed from the conveyance device 70 to the receiving position of the conveyance device 30, the existence of the specimen container 51 (rack 50) is detected (S106 (S205): YES), and the processes after S102 (S202) are executed. The user then simply makes an input of the start instruction through the measurement device 60, sets the specimen container 51 (rack 50) in the conveyance device 70 and starts the measurement to execute the measurement by the specimen examination apparatus 1 and suppress the power consumption by the specimen examination apparatus 1.

In the two embodiments described above, urine has been described for the measurement target, but the blood may also be the measurement target. In other words, the present invention can be applied even to the specimen examination apparatus for examining blood, and furthermore, the present invention can be applied to the specimen examination apparatus for examining other specimens.

Moreover, the present invention can be applied to other clinical specimen processing devices for aspirating and processing the clinical specimen in addition to the clinical specimen examination apparatus described above. For instance, the present invention can be applied to a smear creating device for aspirating and sending blood, applying the blood on the preparation, and creating a sample for microscope observation.

In the two embodiments described above, the pause state is a state in which the power supply to the pneumatic source is stopped, but may be a state in which the power supply to other configuring units is stopped in the measurement device 10 and the conveyance device 30, and simply needs to be a state in which the consumption of power is less than the normal usage state. The other configuring units include a warming mechanism for warming the specimen, the reagent, and the like, or a cooling mechanism for cooling the specimen, the reagent, and the like.

In the two embodiments described above, the display informing "pause state is automatically released, and aspiration task of the specimen is started" is displayed on the display unit 12 of the information processing device 20 when the aspirating operation is automatically started after the release of the pause state, but such notification may not be notified to the user by display and may be notified by voice. The user then can recognize such notification by voice even during the task that requires attention.

Furthermore, the pause state is released according to the existence of the specimen container 51 (rack 50) at the receiving positioning the resuming processes 3 to 6, but the pause state may be released when the specimen container 51 (rack 50) arrives at an arbitrary position on the conveyance path from the receiving position to the aspirating position. For instance, the pause state may be released when the arrival of the specimen container 51 (rack 50) at the most back side position of the right bath region 31a is detected by the switch 35. In this case, the specimen container 51 (Rack 50) is conveyed when the setting to the receiving position is detected by the sensor 32, and thereafter, the pause state is released according to the detection by the switch 35 that the specimen container 51 (rack 50) arrived at the most back side position of the right bath region 31a.

Various modifications may be appropriately made on the embodiments of the present invention within the scope of the technical idea disclosed in the accompanied claims.

For instance, the specimen examination apparatus of the two embodiments described above is configured to convey the specimen to the aspirating position by means of the conveyance device 30, but the present invention may be applied to a specimen examination apparatus in which the conveyance device is not arranged and the user sets the specimen container at the aspirating position.

The specimen examination apparatus of the two embodiments described above is configured to convey the specimen to the aspirating position of the conveyance path 31 by means of the conveyance device 30, and aspirate the specimen using the nozzle 11 from the specimen container 51 at the aspirating position. However, the conveyance device 30 may convey the specimen container 51 to a predetermined position (specimen container acquiring position) near the measurement device 10, retrieve the specimen container 51 positioned at the specimen container acquiring position into the measurement device 10 by means of the measurement device 10, and aspirate the specimen in the specimen container 51 inside the measurement device 10. In this case, the step S107, S206, S311, or S410 (conveyance of specimen container to aspirating position) of the resuming processes 1 to 9 may be replaced with the step of conveying the specimen container to the specimen container acquiring position, and step S108, S208, S312, or S412 (aspiration of specimen) may be replaced with the step of retrieving and aspirating the specimen container at the specimen container retrieving position into the measurement device 10.

In the two embodiments described above, the existence of the specimen container is indirectly detected by detecting the existence of the rack 50 by means of the sensor 32, but the existence of the specimen container 51 may be directly detected by the sensor 32. In this case, the sensor 32 may be arranged by the number of specimen containers that can be set in the rack 50, or only one sensor 32 may be arranged and the existence of the specimen container may be detected when the rack 50 is conveyed.

What is claimed is:

1. A specimen processing device comprising:
    a conveyance unit configured to convey a specimen container accommodating a specimen;
    a processing unit configured to aspirate the specimen by a nozzle from the specimen container conveyed by the conveyance unit, and to process the aspirated specimen, the processing unit including the nozzle, a fluid unit and a pneumatic source respectively connected to the nozzle and the fluid unit, the pneumatic source comprising a positive pressure source and a negative pressure source;
    an instruction accepting section configured to receive an input by a user and output an instruction to start processing of the specimen;
    a sensor configured to detect existence of the specimen container at a position on a conveyance path on which the conveyance unit conveys the specimen container, and output a detection signal; and
    a controller programmed to perform instructions comprising:
    upon detection of no operation of the processing unit for a predetermined time, controlling the processing unit to undergo transition to a pause state, the pause state being a state in which supply of power to the pneumatic source is stopped; and
    releasing the processing unit from the pause state to make the processing unit perform the processing of specimen in response to receiving the instruction to start the processing of the specimen is accepted; from the instruction accepting section or in response to receiving the detection signal from the sensor; and
    controlling the conveyance unit to convey the specimen container based on receiving the detection signal from the sensor,
    wherein the fluid unit comprises a chamber connected to a reagent container accommodating a reagent through a flow path, the pneumatic source respectively supplies pressure to the nozzle and the fluid unit, the nozzle aspirates the specimen and supplies the aspirated specimen to the chamber by the pressure of the pneumatic source, and the reagent is supplied to the chamber by the pressure of the pneumatic source.

2. The specimen processing device according to claim 1, wherein the controller is programmed to:
    control the conveyance unit so as to convey the specimen container to the aspirating position after accepting the instruction to start the processing; and
    control the processing unit to aspirate the specimen from the specimen container conveyed to the aspirating position, and processes the aspirated specimen by the reagent to prepare a measurement sample.

3. The specimen processing device according to claim 2, wherein the controller is programmed to control the conveyance unit so as to convey the specimen container to the aspirating position when the instruction to start the processing is accepted by the instruction accepting section, and the release of the processing unit from the pause state is completed.

4. The specimen processing device according to claim 2, wherein the controller is programmed to control the conveyance unit so as to convey the specimen container to the aspirating position before the release of the processing unit from the pause state is completed when accepting the instruction to start the processing.

5. The specimen processing device according to claim 4, wherein the controller is programmed to:
    determine whether or not the release of the processing unit from the pause state is completed;
    control the processing unit to withhold aspirating the specimen when determined that the release from the pause state is not completed when the specimen container is conveyed to the aspirating position.

6. The specimen processing device according to claim 1, wherein
    the controller is programmed to release the processing unit from the pause state to make the processing unit perform the processing when the instruction to start the processing is accepted and the detection signal from the sensor is received.

7. The specimen processing device according to claim 1, further comprising an informing section, wherein the controller is programmed to inform that the processing of the specimen is automatically performed based on the acceptance of the instruction to start the processing.

8. The specimen processing device according to claim 1, wherein the controller is programmed to:
monitor an operation status of the processing unit; and
make the processing unit undergo transition to the pause state when the processing unit is not operating for a predetermined period.

9. The specimen processing device according to claim 1, wherein the fluid unit further comprises a diaphragm pump which draws the reagent from the reagent container by negative pressure from the negative pressure source of the pneumatic source and supplies the drawn reagent to the chamber by positive pressure from the positive pressure source of the pneumatic source.

10. The specimen processing device according to claim 1, wherein the controller programmed to:
control the conveyance unit to convey a specimen container to a specimen container acquiring position for acquiring the container by the processing unit; and
control the conveyance unit so as to convey the specimen container to the specimen container acquiring position based on the acceptance of the instruction to start the processing; wherein
the processing unit is configured to transport the specimen container conveyed to the specimen container acquiring position to an aspirating position for aspirating the specimen in the specimen container, aspirate the specimens from the specimen container transported to the aspirating position, and process the aspirated specimen with the reagent to prepare the measurement sample.

11. A specimen processing device comprising:
a conveyance unit configured to convey a specimen container accommodating a specimen;
a processing unit configured to aspirate the specimen by a nozzle from the specimen container conveyed by the conveyance unit, and to process the aspirated specimen, the processing unit including the nozzle, a fluid unit and a pneumatic source respectively connected to the nozzle and the fluid unit, the pneumatic source comprising a positive pressure source and a negative pressure source;
a sensor configured to detect existence of the specimen container at a predetermined position on a conveyance path on which the conveyance unit conveys the specimen, and output a detection signal; and
a controller programmed to perform instructions comprising:
upon detection of no operation of the processing unit for a predetermined time, controlling the processing unit to undergo transition to a pause state, the pause state being a state in which supply of power to the pneumatic source is stopped;
receiving the detection signal from the sensor; and
releasing the processing unit from the pause state in response to receiving the detection signal from the sensor,
wherein the fluid unit comprises a chamber connected to a reagent container accommodating a reagent through a flow path, the pneumatic source respectively supplies pressure to the nozzle and the fluid unit, the nozzle aspirates the specimen and supplies the aspirated specimen to the chamber by the pressure of the pneumatic source, and the reagent is supplied to the chamber by the pressure of the pneumatic source.

12. The specimen processing device according to claim 11, wherein the fluid unit further comprises a diaphragm pump which draws the reagent from the reagent container by negative pressure from the negative pressure source of the pneumatic source and supplies the drawn reagent to the chamber by positive pressure from the positive pressure source of the pneumatic source.

13. The specimen processing device according to claim 11, wherein the controller is programmed to:
control the conveyance unit so as to convey the specimen container to an aspirating position based on receiving the detection signal from the sensor; and
control the processing unit to aspirate the specimen from the specimen container at the aspirating position.

14. The specimen processing device according to claim 13, wherein the controller is programmed to control the conveyance unit so as to convey the specimen container to the aspirating position when the detection signal from the sensor is received and the release of the processing unit from the pause state is completed.

15. The specimen processing device according to claim 13, wherein the controller is configured to control the conveyance unit so as to convey the specimen container to the aspirating position before the release of the processing unit from the pause state is completed when the detection signal from the sensor is received.

16. The specimen processing device according to claim 15, wherein the controller is programmed to:
determine whether or not the release of the processing unit from the pause state is completed;
control the processing unit to withhold aspirating the specimen when determined that the release from the pause state is not completed when the specimen container is conveyed to the aspirating position.

17. The specimen processing device according to claim 11, further comprising an informing section, wherein
the controller is programmed to control the informing section to inform that the processing of the specimen is automatically performed based on the receiving the detection signal from the sensor.

18. The specimen processing device according to claim 11, wherein the controller is programmed to:
set the control of the conveyance unit to an automatic conveyance mode of conveying the specimen container if the specimen container exists at the predetermined position and a conveyance stop mode of not conveying the specimen container even if the specimen container exists at the predetermined position; wherein
the controller is configured not to release the processing unit from the pause state regardless of the receiving the detection signal from the sensor when the control of the conveyance unit is set to the conveyance stop mode.

19. The specimen-processing device according to claim 18, wherein the sensor is configured not to perform the detection of the specimen container at the predetermined position when the control of the conveyance unit is set to the conveyance stop mode.

20. The specimen processing device according to claim 18, further comprising:
an instruction accepting section configured to receive an input by a user and output an instruction to start processing of the specimen; wherein
the controller is programmed to set the control of the conveyance unit to the automatic conveyance mode when accepting the instruction to start the processing if the control of the conveyance unit is set to the conveyance stop mode.

21. The specimen processing device according to claim 18, further comprising:
a cancel instruction accepting section configured to receive an input by a user and output an instruction to cancel the processing of the specimen, which processing started; wherein
the controller is programmed to set the control of the conveyance unit to the conveyance stop mode when receiving the instruction to cancel the processing if the control of the conveyance unit is set to the automatic conveyance mode.

22. The specimen processing device according to claim 11, wherein the controller is programmed to:
monitor an operation status of the processing unit; and
make the processing unit undergo transition to the pause state when the processing unit is not operating for a predetermined period.

23. The specimen processing device according to claim 11, wherein:
the conveyance unit is configured to convey the specimen container accommodating a specimen to a predetermined position; and
the processing unit is configured to acquire the specimen container conveyed to the predetermined position, aspirate the specimen from the specimen container, and process the aspirated specimen with the reagent to prepare the measurement sample.

24. A specimen-processing device comprising:
a conveyance unit configured to convey a specimen container accommodating a specimen;
a processing unit configured to aspirate the specimen by a nozzle from the specimen container conveyed by the conveyance unit, and to process the aspirated specimen, the processing unit including the nozzle, a fluid unit and a pneumatic source respectively connected to the nozzle and the fluid unit, the pneumatic source comprising a positive pressure source and a negative pressure source;
an instruction accepting section configured to receive an input by a user and output an instruction to start processing of the specimen; and
a controller programmed to perform instructions comprising:
upon detection of no operation of the processing unit for a predetermined time, controlling the processing unit to undergo transition to a pause state, the pause state being a state in which supply of power to the pneumatic source is stopped, whereby power consumption of the pneumatic source and noises caused by driving the pneumatic source are reduced;
receiving, from the instruction accepting section, the instruction to start processing of the specimen when the processing unit is in the pause state; and
releasing the processing unit from the pause state to make the processing unit perform the processing of specimen in response to receiving the instruction to start the processing is accepted, whereby aspirating the specimen and processing the aspirated specimen can be performed without an additional instruction subsequent to the instruction to start processing of the specimen,
wherein the fluid unit comprises a chamber connected to a reagent container accommodating a reagent through a flow path, the pneumatic source respectively supplies pressure to the nozzle and the fluid unit, the nozzle aspirates the specimen and supplies the aspirated specimen to the chamber by the pressure of the pneumatic source, and the reagent is supplied to the chamber by the pressure of the pneumatic source.

25. A specimen processing device comprising:
a conveyance unit configured to convey a specimen container accommodating a specimen;
a processing unit configured to aspirate the specimen by a nozzle from the specimen container conveyed by the conveyance unit, and to process the aspirated specimen, the processing unit including the nozzle, a fluid unit and a pneumatic source respectively connected to the nozzle and the fluid unit, the pneumatic source comprising a positive pressure source and a negative pressure source;
an instruction accepting section configured to receive an input by a user and output an instruction to start processing of the specimen;
a sensor configured to detect existence of the specimen container at a position on a conveyance path on which the conveyance unit conveys the specimen container, and output a detection signal; and
a controller programmed to perform instructions comprising:
upon detection of no operation of the processing unit for a predetermined time, controlling the processing unit to undergo transition to a pause state, the pause state being a state in which supply of power to the pneumatic source is stopped, whereby power consumption of the pneumatic source and noises caused by driving the pneumatic source are reduced;
receiving selection of one of a first mode of operation and a second mode of operation, wherein the selection of the first mode is performed by receiving, from the instruction accepting section, the instruction to start processing of the specimen when the processing unit is in the pause state and the selection of the second mode is performed by receiving the detection signal from the sensor when the processing unit is in the pause state;
upon selection of the first mode:
in response to receiving the instruction to start processing of the specimen, releasing the processing unit from the pause state to make the processing unit perform the processing of specimen, whereby aspirating the specimen and processing the aspirated specimen can be performed without an additional instruction subsequent to the instruction to start processing of the specimen, and
upon selection of the second mode:
in response to receiving the detection signal that detects the specimen container, releasing the processing unit from the pause state to make the processing unit perform the processing of the specimen,
wherein the fluid unit comprises a chamber connected to a reagent container accommodating a reagent through a flow path, the pneumatic source respectively supplies pressure to the nozzle and the fluid unit, the nozzle aspirates the specimen and supplies the aspirated specimen to the chamber by the pressure of the pneumatic source, and the reagent is supplied to the chamber by the pressure of the pneumatic source.

* * * * *